(12) United States Patent
Brummerhop et al.

(10) Patent No.: US 8,748,483 B2
(45) Date of Patent: Jun. 10, 2014

(54) USE OF SUBSTITUTED PYRANONE ACID DERIVATIVES FOR THE TREATMENT OF METABOLIC SYNDROME

(75) Inventors: Harm Brummerhop, Frankfurt am Main (DE); Siegfried Stengelin, Frankfurt am Main (DE); Hubert Heuer, Frankfurt am Main (DE); Susanne Kilp, Hergenfeld (DE); Andreas Herling, Frankfurt am Main (DE); Thomas Klabunde, Frankfurt am Main (DE); Dieter Kadereit, Frankfurt am Main (DE); Matthias Urmann, Frankfurt am Main (DE)

(73) Assignee: SANOFI, Paris (FR)

( * ) Notice: Subject to any disclaimer, the term of this patent is extended or adjusted under 35 U.S.C. 154(b) by 696 days.

(21) Appl. No.: 12/504,198

(22) Filed: Jul. 16, 2009

(65) Prior Publication Data

US 2010/0144862 A1   Jun. 10, 2010

Related U.S. Application Data

(63) Continuation of application No. PCT/EP2008/000029, filed on Jan. 4, 2008.

(30) Foreign Application Priority Data

Jan. 16, 2007   (DE) .......................... 10 2007 002 260

(51) Int. Cl.
    *A01N 43/16* (2006.01)
    *A61K 31/35* (2006.01)
    *C09B 3/00* (2006.01)
    *C07D 209/80* (2006.01)
    *C09B 7/00* (2006.01)

(52) U.S. Cl.
    USPC ........................... 514/460; 549/417; 549/420

(58) Field of Classification Search
    USPC .................................. 514/460; 549/417, 420
    See application file for complete search history.

(56) References Cited

U.S. PATENT DOCUMENTS

| 3,152,148 | A  | 10/1964 | Easterly et al. |
|-----------|----|---------|-----------------|
| 6,221,633 | B1 | 4/2001  | Ertl et al.     |
| 6,221,897 | B1 | 4/2001  | Frick et al.    |
| 6,245,744 | B1 | 6/2001  | Frick et al.    |
| 6,342,512 | B1 | 1/2002  | Kirsch et al.   |
| 6,498,156 | B2 | 12/2002 | Glombik et al.  |
| 6,552,073 | B1 | 4/2003  | Leblanc et al.  |

FOREIGN PATENT DOCUMENTS

| DE | 195 30 298 A1 | 2/1997 |
|----|---------------|--------|
| EP | 0 006 749     | 1/1980 |
| EP | 0 114 531 A1  | 8/1984 |
| EP | 0 171 814 A1  | 2/1986 |
| EP | 0 305 814 A2  | 3/1989 |
| EP | 0 305 815 A2  | 3/1989 |
| EP | 0 305 816 A2  | 3/1989 |
| EP | 0 462 884 A1  | 12/1991 |
| EP | 0 912 520     | 1/1998 |
| EP | 0 400 269 A2  | 4/2011 |
| GB | 2 192 130 A   | 2/1986 |
| JP | 06271500      | * 9/1994 |
| WO | WO 97/26265   | 7/1997 |
| WO | WO 97/41097   | 11/1997 |
| WO | WO 98/08871   | 3/1998 |
| WO | WO 99/03861   | 1/1999 |
| WO | WO 99/15525   | 4/1999 |
| WO | WO 00/40569   | 7/2000 |
| WO | WO 00/63208   | 10/2000 |
| WO | WO 00/66585   | 11/2000 |
| WO | WO 00/71549 A1 | 11/2000 |
| WO | WO 00/78312 A1 | 12/2000 |
| WO | WO 01/09111 A1 | 2/2001 |
| WO | WO 01/83451 A1 | 11/2001 |
| WO | WO 01/85695 A1 | 11/2001 |
| WO | WO 01/91752 A1 | 12/2001 |
| WO | WO 02/28346 A2 | 4/2002 |
| WO | WO 03/020269 A1 | 3/2003 |

OTHER PUBLICATIONS

Grundy (Nature Reviews: Drug Discovery, vol. 5, p. 295-309, 2006).*
Cecil Textbook of Medicine, 1996, p. 1004-1010.*
Golub, Science 286, p. 531-537, 1999.*
Hurst et al. (Annals of Internal Medicine, 2003, 825-837).*
Asakawa, A. et al., "Cocaine-Amphetamine-Regulated Transcript Influences Energy Metabolism, Anxiety and Gastric Emptying in Mice," Hormone and Metabolic Research (2001), vol. 33, pp. 554-558.
Pershin, G.N. et al., "Chemotherapeutic effectiveness of stibomen in experimental leishmaniasis and trypanosomiasis," Abstract aus Chemical Abstracts Datenbank, CA 1968:1897, Meditsinkskaya Parazitologiya i Parazitarnye Bolezni (1967), vol. 36, pp. 422-427.
Hauner, Von. H., "Neue Definition des Metabolischen Syndroms: Wo fangt die Krankheit an?" MMW-Fortschr.Med. Nr. (2006), vol. 49-50, pp. 42-44.
Salvador, Javier et al., "Perspectives in the therapeutic use of leptin," Expert Opinion on Pharmacotherapy (2001), vol. 2, pp. 1615-1629.
Lee, Daniel W. et al., "Leptin agonists as a potential approach to the treatment of obesity," Drugs of the Future (2001), vol. 26, pp. 873-881.

(Continued)

*Primary Examiner* — Uma Ramachandran
(74) *Attorney, Agent, or Firm* — Scully, Scott, Murphy & Presser, P.C.

(57) ABSTRACT

The invention relates to the use of substituted pyranone acid derivatives and of their physiologically acceptable salts for producing medicaments for treating the metabolic syndrome.

5 Claims, No Drawings

(56) References Cited

OTHER PUBLICATIONS

Sammes, Michael P. et al., "Synthetic Applications of N—N Linked Heterocycles. Part 12. The preparation of 4-Alkylthio- and 4-Arylthio-pyridines by Regiospecific Attack of Thioalkoxide Ions on N-(4-Oxopyridin-1-yl)pyridinium Salts," Perkin Transactions (1981), pp. 1585-1590.

Pace, Paola et al., "The monoethyl ester of meconic acid is an active site inhibtor of HCV NS5B RNA-dependent RNA polymerase," Bioorganic and Medicinal Chemistry Letters (2004), vol. 14, pp. 3257-3261.

Tyle, Praveen, "Iontophoretic Devices for Drug Delivery," Pharmaceutical Research (1986), vol. 3, pp. 318-326.

Offermanns, Stefan, "The nicotinic acid receptor GPR109A (HM74A or PUMA-G) as a new therapeutic target," Trends in Pharmacological Sciences (2006), vol. 27, pp. 384-390.

Zunft, H.J.F. et al., "Carob Pulp Preparation for Treatment of Hypercholesterolemia," Advances in Therapy (2001), vol. 18, pp. 230-236.

Rote Liste 2006, Kapitel 12.

* cited by examiner

USE OF SUBSTITUTED PYRANONE ACID DERIVATIVES FOR THE TREATMENT OF METABOLIC SYNDROME

The invention relates to the use of substituted pyranone acid derivatives and of their physiologically acceptable salts for producing medicaments for treating the metabolic syndrome.

U.S. Pat. No. 6,552,073 describes pyranone acid derivatives of a similar structure having an antiproliferative action.

The invention was based on the object of providing compounds which can be used for the treatment of the metabolic syndrome and which display in particular a therapeutically useful lipid-lowering effect. It was further intended preferably that they be suitable for the treatment of diabetic dyslipidemia. It was further intended preferably that a reduction in the free fatty acids (FFA), of glycerol and of triglycerides in the plasma be achieved.

The invention therefore relates to the use of compounds of the formula I

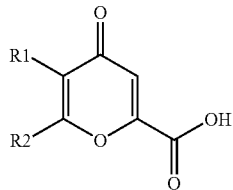

in which

R1 is H, F, Cl, Br, I, OH, $CF_3$, $NO_2$, CN, $OCF_3$, $NH_2$, $NH(C_1$-$C_6)$-alkyl, $N((C_1$-$C_6)$-alkyl$)_2$, $SF_5$, $SO_2$—$CH_3$, COOH, COO—$(C_1$-$C_6)$-alkyl, $CONH_2$, $(C_1$-$C_{20})$-alkyl, $(C_3$-$C_{20})$-cycloalkyl, $(C_2$-$C_{20})$-alkenyl, $(C_2$-$C_{20})$-alkynyl, aryl, heterocycle, where in the $(C_1$-$C_{20})$-alkyl and $(C_2$-$C_{20})$-alkenyl radicals one or more individual —$CH_2$— or —CH— groups may be replaced by —O— and where the alkyl, cycloalkyl, alkenyl, alkynyl, aryl- and heterocyclyl radicals may be mono- or polysubstituted by F, Cl, Br, I, $CF_3$, $NO_2$, $N_3$, CN, =O, COOH, COO($C_1$-$C_6$)-alkyl, $CONH_2$, $CONH(C_1$-$C_6)$-alkyl, $CON[(C_1$-$C_6)$-alkyl$]_2$, cycloalkyl, $(C_1$-$C_{10})$-alkyl, $(C_2$-$C_6)$-alkenyl, $(C_2$-$C_6)$-alkynyl, O—$(C_1$-$C_6)$-alkyl, O—CO—$(C_1$-$C_6)$-alkyl, O—CO—$(C_1$-$C_6)$-aryl, O—CO—$(C_1$-$C_6)$-heterocyclyl;

$PO_3H_2$, P(O)(Oalkyl$)_2$, $(C_1$-$C_6)$-alkylene-P(O)(Oalkyl$)_2$, O—P(O)(OH$)_2$, O—P(O)(Oalkyl$)_2$, $SO_3H$, $SO_2$—$NH_2$, $SO_2NH(C_1$-$C_6)$-alkyl, $SO_2N[(C_1$-$C_6)$-alkyl$]_2$, S—$(C_1$-$C_6)$-alkyl, S—$(CH_2)_n$-aryl, S—$(CH_2)_n$-heterocyclyl, SO—$(C_1$-$C_6)$-alkyl, SO—$(CH_2)_n$-aryl, SO—$(CH_2)_n$-heterocyclyl, $SO_2$—$(C_1$-$C_6)$-alkyl, $SO_2$—$(CH_2)_n$-aryl, $SO_2$—$(CH_2)_n$-heterocyclyl, $SO_2$—$NH(CH_2)_n$-aryl, $SO_2$—$NH(CH_2)_n$-heterocyclyl, $SO_2$—$N((C_1$-$C_6)$-alkyl)$(CH_2)_n$-aryl, $SO_2$—$N((C_1$-$C_6)$-alkyl)$(CH_2)_n$-heterocyclyl, $SO_2$—$N((CH_2)_n$-aryl$)_2$, $SO_2$—$N((CH_2)_n$-heterocyclyl$)_2$ where n=0-6 and the aryl radical or heterocyclic radical may be substituted up to two times by F, Cl, Br, OH, $CF_3$, $SF_5$, $NO_2$, CN, $OCF_3$, C—$(C_1$-$C_6)$-alkyl, $(C_1$-$C_6)$-alkyl, $NH_2$;

$C(NH)(NH_2)$, $NH_2$, NH—$(C_1$-$C_6)$-alkyl, $N((C_1$-$C_6)$-alkyl$)_2$, $NH(C_1$-$C_7)$-acyl, NH—CO—$(C_1$-$C_6)$-alkyl, NH—COO—$(C_1$-$C_6)$-alkyl, NH—CO-aryl, NH—CO-heterocyclyl, NH—COO-aryl, NH—COO-heterocyclyl, NH—CO—NH—$(C_1$-$C_6)$-alkyl), NH—CO—NH-aryl, NH—CO—NH-heterocyclyl, N[$(C_1$-$C_6)$-alkyl]-CO—$(C_1$-$C_6)$-alkyl, N[$(C_1$-$C_6)$-alkyl]-COO—$(C_1$-$C_6)$-alkyl, N[$(C_1$-$C_6)$-alkyl]-CO-aryl, N[$(C_1$-$C_6)$-alkyl]-CO-heterocyclyl, N[$(C_1$-$C_6)$-alkyl]-COO-aryl, N[$(C_1$-$C_6)$-alkyl]-COO-heterocyclyl, N[$(C_1$-$C_6)$-alkyl]-CO—NH—$(C_1$-$C_6)$-alkyl), N[$(C_1$-$C_6)$-alkyl]-CO—NH-aryl, N[$(C_1$-$C_6)$-alkyl]-CO—NH-heterocyclyl, N[$(C_1$-$C_6)$-alkyl]-CO—N$((C_1$-$C_6)$-alkyl$)_2$, N[$(C_1$-$C_6)$-alkyl]-CO—N$((C_1$-$C_6)$-alkyl)-aryl, N[$(C_1$-$C_6)$-alkyl]-CO—N$((C_1$-$C_6)$-alkyl)-heterocyclyl, N[$(C_1$-$C_6)$-alkyl]-CO—N(aryl$)_2$, N[$(C_1$-$C_6)$-alkyl]-CO—N(heterocyclyl$)_2$, N(aryl)-CO—$(C_1$-$C_6)$-alkyl, N(heterocyclyl)-CO—$(C_1$-$C_6)$-alkyl, N(aryl)-COO—$(C_1$-$C_6)$-alkyl, N(heterocyclyl)-COO—$(C_1$-$C_6)$-alkyl, N(aryl)—CO-aryl, N(heterocyclyl)-CO-aryl, N(aryl)-COO-aryl, N(heterocyclyl)-COO-aryl, N(aryl)-CO—NH—$(C_1$-$C_6)$-alkyl, N(heterocyclyl)-CO—NH—$(C_1$-$C_6)$-alkyl, N(aryl)-CO—NH-aryl, N(heterocyclyl)-CO—NH-aryl, N(aryl)-CO—N$((C_1$-$C_6)$-alkyl$)_2$, N(heterocyclyl)-CO—N$((C_1$-$C_6)$-alkyl$)_2$, N(aryl)-CO—N[$(C_1$-$C_6)$-alkyl]-aryl, N(heterocyclyl)-CO—N[$(C_1$-$C_6)$-alkyl]-aryl, N(aryl)-CO—N(aryl$)_2$, N(heterocyclyl)-CO—N(aryl$)_2$, aryl, O—$(CH_2)_n$-aryl, O—$(CH_2)_n$-heterocyclyl, where n=0-6 and where the aryl or heterocyclyl radical may be mono- to trisubstituted by F, Cl, Br, I, OH, $CF_3$, $NO_2$, CN, $OCF_3$, O—$(C_1$-$C_6)$-alkyl, $(C_1$-$C_6)$-alkyl, $NH_2$, $NH(C_1$-$C_6)$-alkyl, $N((C_1$-$C_6)$-alkyl$)_2$, $SF_5$, $SO_2$—$CH_3$, COOH, COO—$(C_1$-$C_6)$-alkyl, $CONH_2$;

R2 is H, F, Cl, Br, I, OH, $CF_3$, $NO_2$, CN, $OCF_3$, $NH_2$, $NH(C_1$-$C_6)$-alkyl, $N((C_1$-$C_6)$-alkyl$)_2$, $SF_5$, $SO_2$—$CH_3$, COOH, COO—$(C_1$-$C_6)$-alkyl, $CONH_2$, $(C_1$-$C_{20})$-alkyl, $(C_3$-$C_{20})$-cycloalkyl, $(C_2$-$C_{20})$-alkenyl, $(C_2$-$C_{20})$-alkynyl, aryl, heterocycle, where in the $(C_1$-$C_{20})$-alkyl and $(C_2$-$C_{20})$-alkenyl radicals one or more individual —$CH_2$— or —CH— groups may be replaced by —O— and where the alkyl, cycloalkyl, alkenyl, alkynyl, aryl and heterocyclyl radicals may be mono- or polysubstituted by F, Cl, Br, I, $CF_3$, $NO_2$, $N_3$, CN, =O, COOH, COO($C_1$-$C_6$)-alkyl, $CONH_2$, $CONH(C_1$-$C_6)$-alkyl, $CON[(C_1$-$C_6)$-alkyl$]_2$, cycloalkyl, $C_{10})$-alkyl, $(C_2$-$C_6)$-alkenyl, $(C_2$-$C_6)$-alkynyl, O—$(C_1$-$C_6)$-alkyl, O—CO—$(C_1$-$C_6)$-alkyl, O—CO—$(C_1$-$C_6)$-aryl, O—CO—$(C_1$-$C_6)$-heterocyclyl;

$PO_3H_2$, P(O)(Oalkyl$)_2$, $(C_1$-$C_6)$-alkylene-P(O)(Oalkyl$)_2$, O—P(O)(OH$)_2$, O—P(O)(Oalkyl$)_2$, $SO_3H$, $SO_2$—$NH_2$, $SO_2NH(C_1$-$C_6)$-alkyl, $SO_2N[(C_1$-$C_6)$-alkyl$]_2$, S—$(C_1$-$C_6)$-alkyl, S—$(CH_2)_n$-aryl, S—$(CH_2)_n$-heterocyclyl, SO—$(C_1$-$C_6)$-alkyl, SO—$(CH_2)_n$-aryl, SO—$(CH_2)_n$-heterocyclyl, $SO_2$—$(C_1$-$C_6)$-alkyl, $SO_2$—$(CH_2)_n$-aryl, $SO_2$—$(CH_2)_n$-heterocyclyl, $SO_2$—$NH(CH_2)_n$-aryl, $SO_2$—$NH(CH_2)_n$-heterocyclyl, $SO_2$—$N((C_1$-$C_6)$-alkyl)$(CH_2)_n$-aryl, $SO_2$—$N((C_1$-$C_6)$-alkyl)$(CH_2)_n$-heterocyclyl, $SO_2$—$N((CH_2)_n$-aryl$)_2$, $SO_2$—$N((CH_2)_n$-heterocyclyl$)_2$ where n=0-6 and the aryl radical or heterocyclic radical may be substituted up to two times by F, Cl, Br, OH, $CF_3$, $SF_5$, $NO_2$, CN, $OCF_3$, O—$(C_1$-$C_6)$-alkyl, $(C_1$-$C_6)$-alkyl, $NH_2$;

$C(NH)(NH_2)$, $NH_2$, NH—$(C_1$-$C_6)$-alkyl, $N((C_1$-$C_6)$-alkyl$)_2$, $NH(C_1$-$C_7)$-acyl, NH—CO—$(C_1$-$C_6)$-alkyl, NH—COO—$(C_1$-$C_6)$-alkyl, NH—CO-aryl, NH—CO-heterocyclyl, NH—COO-aryl, NH—COO-heterocyclyl, NH—CO—NH—$(C_1$-$C_6)$-alkyl), NH—CO—NH-aryl, NH—CO—NH-heterocyclyl, N[$(C_1$-$C_6)$-alkyl]-CO—$(C_1$-$C_6)$-alkyl, N[$(C_1$-$C_6)$-alkyl]-COO—$(C_1$-$C_6)$-alkyl, N[$(C_1$-$C_6)$-alkyl]-CO-aryl, N[$(C_1$-$C_6)$-alkyl]-CO-heterocyclyl, N[$(C_1$-$C_6)$-alkyl]-COO-aryl, N[$(C_1$-$C_6)$-alkyl]-COO-heterocyclyl, N[$(C_1$-$C_6)$-alkyl]-CO—

NH—($C_1$-$C_6$)-alkyl), N[($C_1$-$C_6$)-alkyl]-CO—NH-aryl, N[($C_1$-$C_6$)-alkyl]-CO—NH-heterocyclyl, N[($C_1$-$C_6$)-alkyl]-CO—N(($C_1$-$C_6$)-alkyl)$_2$, N[($C_1$-$C_6$)-alkyl]-CO—N(($C_1$-$C_6$)-alkyl)-aryl, N[($C_1$-$C_6$)-alkyl]-CO—N(($C_1$-$C_6$)-alkyl)-heterocyclyl, N[($C_1$-$C_6$)-alkyl]-CO—N(aryl)$_2$, N[($C_1$-$C_6$)-alkyl]-CO—N(heterocyclyl)$_2$, N(aryl)-CO—($C_1$-$C_6$)-alkyl, N(heterocyclyl)-CO—($C_1$-$C_6$)-alkyl, N(aryl)-COO—($C_1$-$C_6$)-alkyl, N(heterocyclyl)-COO—($C_1$-$C_6$)-alkyl, N(aryl)-CO-aryl, N(heterocyclyl)-CO-aryl, N(aryl)-COO-aryl, N(heterocyclyl)-COO-aryl, N(aryl)-CO—NH—($C_1$-$C_6$)-alkyl, N(heterocyclyl)-CO—NH—($C_1$-$C_6$)-alkyl, N(aryl)-CO—NH-aryl, N(heterocyclyl)-CO—NH-aryl, N(aryl)-CO—N(($C_1$-$C_6$)-alkyl)$_2$, N(heterocyclyl)-CO—N(($C_1$-$C_6$)-alkyl)$_2$, N(aryl)-CO—N[($C_1$-$C_6$)-alkyl]-aryl, N(heterocyclyl)-CO—N[($C_1$-$C_6$)-alkyl]-aryl, N(aryl)-CO—N(aryl)$_2$, N(heterocyclyl)-CO—N(aryl)$_2$, aryl, O—($CH_2$)$_n$-aryl, O—($CH_2$)$_n$-heterocyclyl, where n=0-6 and where the aryl or heterocyclyl radical may be mono- to trisubstituted by F, Cl, Br, I, OH, $CF_3$, $NO_2$, CN, $OCF_3$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SF_5$, $SO_2$—$CH_3$, COOH, COO—($C_1$-$C_6$)-alkyl, $CONH_2$, or R1 and R2 together form a 3- to 8-membered aryl, cycloalkyl or heterocyclyl ring, where the aryl, cycloalkyl or heterocyclyl ring may be substituted by F, Cl, Br, I, OH, $CF_3$, $NO_2$, CN, $OCF_3$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SF_5$, $SO_2$—$CH_3$, COOH, COO—($C_1$-$C_6$)-alkyl, $CONH_2$ and where the aryl, cycloalkyl or heterocyclyl ring may be fused to a further aryl, cycloalkyl or heterocyclyl ring;

and physiologically acceptable salts thereof.

Preference is given to using the compounds of the formula I in which

R1 is H, OH, COOH, ($C_1$-$C_8$)-alkyl, ($C_2$-$C_8$)-alkenyl, aryl, where in the ($C_1$-$C_8$)-alkyl and ($C_2$-$C_8$)-alkenyl radicals one or more individual —$CH_2$— or —CH— groups may be replaced by —O— and where the alkyl, alkenyl and aryl radicals may be mono- or polysubstituted by F, Cl, Br, I, $CF_3$, $NO_2$, $N_3$, CN, =O, COOH, COO($C_1$-$C_6$)-alkyl, $CONH_2$, CONH($C_1$-$C_6$)-alkyl, CON[($C_1$-$C_6$)-alkyl]$_2$, cycloalkyl, ($C_1$-$C_{10}$)-alkyl, ($C_2$-$C_6$)-alkenyl, ($C_2$-$C_6$)-alkynyl, O—($C_1$-$C_6$)-alkyl, O—CO—($C_1$-$C_6$)-alkyl, O—CO—($C_1$-$C_6$)-aryl, O—CO—($C_1$-$C_6$)-heterocyclyl;

$PO_3H_2$, P(O)(Oalkyl)$_2$, ($C_1$-$C_6$)-alkylene-P(O)(Oalkyl)$_2$, O—P(O)(OH)$_2$, O—P(O)(Oalkyl)$_2$, $SO_3H$, $SO_2$—$NH_2$, $SO_2NH$($C_1$-$C_6$)-alkyl, $SO_2N$[($C_1$-$C_6$)-alkyl]$_2$, S—($C_1$-$C_6$)-alkyl, S—($CH_2$)$_n$-aryl, S—($CH_2$)$_n$-heterocyclyl, SO—($C_1$-$C_6$)-alkyl, SO—($CH_2$)$_n$-aryl, SO—($CH_2$)$_n$-heterocyclyl, $SO_2$—($C_1$-$C_6$)-alkyl, $SO_2$—($CH_2$)$_n$-aryl, $SO_2$—($CH_2$)$_n$-heterocyclyl, $SO_2$—NH($CH_2$)$_n$-aryl, $SO_2$—NH($CH_2$)$_n$-heterocyclyl, $SO_2$—N(($C_1$-$C_6$)-alkyl)($CH_2$)$_n$-aryl, $SO_2$—N(($C_1$-$C_6$)-alkyl)($CH_2$)$_n$-heterocyclyl, $SO_2$—N(($CH_2$)$_n$-aryl)$_2$, $SO_2$—N(($CH_2$)$_n$-(heterocyclyl))$_2$ where n=0-6 and the aryl radical or heterocyclic radical may be substituted up to two times by F, Cl, Br, OH, $CF_3$, $SF_5$, $NO_2$, CN, $OCF_3$, O—($C_1$-$C_6$)-alkyl, ($C_1$-$C_6$)-alkyl, $NH_2$;

C(NH)($NH_2$), $NH_2$, NH—($C_1$-$C_6$)-alkyl, N(($C_1$-$C_6$)-alkyl)$_2$, NH($C_1$-$C_7$)-acyl, NH—CO—($C_1$-$C_6$)-alkyl, NH—COO—($C_1$-$C_6$)-alkyl, NH—CO-aryl, NH—CO-heterocyclyl, NH—COO-aryl, NH—COO-heterocyclyl, NH—CO—NH—($C_1$-$C_6$)-alkyl), NH—CO—NH-aryl, NH—CO—NH-heterocyclyl, N[($C_1$-$C_6$)-alkyl]-CO—($C_1$-$C_6$)-alkyl, N[($C_1$-$C_6$)-alkyl]-COO—($C_1$-$C_6$)-alkyl, N[($C_1$-$C_6$)-alkyl]-CO-aryl, N[($C_1$-$C_6$)-alkyl]-CO-heterocyclyl, N[($C_1$-$C_6$)-alkyl]-COO-aryl, N[($C_1$-$C_6$)-alkyl]-COO-heterocyclyl, N[($C_1$-$C_6$)-alkyl]-CO—NH—($C_1$-$C_6$)-alkyl), N[($C_1$-$C_6$)-alkyl]-CO—NH-aryl, N[($C_1$-$C_6$)-alkyl]-CO—NH-heterocyclyl, N[($C_1$-$C_6$)-alkyl]-CO—N(($C_1$-$C_6$)-alkyl)$_2$, N[($C_1$-$C_6$)-alkyl]-CO—N(($C_1$-$C_6$)-alkyl)-aryl, N[($C_1$-$C_6$)-alkyl]-CO—N(($C_1$-$C_6$)-alkyl)-heterocyclyl, N[($C_1$-$C_6$)-alkyl]-CO—N(aryl)$_2$, N[($C_1$-$C_6$)-alkyl]-CO—N(heterocyclyl)$_2$, N(aryl)-CO—($C_1$-$C_6$)-alkyl, N(heterocyclyl)-CO—($C_1$-$C_6$)-alkyl, N(aryl)-COO—($C_1$-$C_6$)-alkyl, N(heterocyclyl)-COO—($C_1$-$C_6$)-alkyl, N(aryl)-CO-aryl, N(heterocyclyl)-CO-aryl, N(aryl)-COO-aryl, N(heterocyclyl)-COO-aryl, N(aryl)-CO—NH—($C_1$-$C_6$)-alkyl, N(heterocyclyl)-CO—NH—($C_1$-$C_6$)-alkyl, N(aryl)-CO—NH-aryl, N(heterocyclyl)-CO—NH-aryl, N(aryl)-CO—N(($C_1$-$C_6$)-alkyl)$_2$, N(heterocyclyl)-CO—N(($C_1$-$C_6$)-alkyl)$_2$, N(aryl)-CO—N[($C_1$-$C_6$)-alkyl]-aryl, N(heterocyclyl)-CO—N[($C_1$-$C_6$)-alkyl]-aryl, N(aryl)-CO—N(aryl)$_2$, N(heterocyclyl)-CO—N(aryl)$_2$, aryl, O—($CH_2$)$_n$-aryl, O—($CH_2$)$_n$-heterocyclyl, where n=0-6 and where the aryl or heterocyclyl radical may be mono- to trisubstituted by F, Cl, Br, I, OH, $CF_3$, $NO_2$, CN, $OCF_3$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SF_5$, $SO_2$—$CH_3$, COOH, COO—($C_1$-$C_6$)-alkyl, $CONH_2$, R2 is H, OH, COOH, ($C_1$-$C_8$)-alkyl, ($C_3$-$C_8$)-cycloalkyl, ($C_2$-$C_8$)-alkenyl, where in the ($C_1$-$C_8$)-alkyl and ($C_2$-$C_8$)-alkenyl radicals one or more individual —$CH_2$— or —CH— groups may be replaced by —O— and where the alkyl, cycloalkyl and alkenyl radicals may be mono- or polysubstituted by F, Cl, Br, I, $CF_3$, $NO_2$, $N_3$, CN, =O, COOH, COO($C_1$-$C_6$)-alkyl, $CONH_2$, CONH($C_1$-$C_6$)-alkyl, CON[($C_1$-$C_6$)-alkyl]$_2$, cycloalkyl, ($C_1$-$C_{10}$)-alkyl, ($C_2$-$C_6$)-alkenyl, ($C_2$-$C_6$)-alkynyl, O—($C_1$-$C_6$)-alkyl, O—CO—($C_1$-$C_6$)-alkyl, O—CO—($C_1$-$C_6$)-aryl, O—CO—($C_1$-$C_6$)-heterocyclyl;

$PO_3H_2$, P(O)(Oalkyl)$_2$, ($C_1$-$C_6$)-alkylene-P(O)(Oalkyl)$_2$, O—P(O)(OH)$_2$, O—P(O)(Oalkyl)$_2$, $SO_3H$, $SO_2$—$NH_2$, $SO_2NH$($C_1$-$C_6$)-alkyl, $SO_2N$[($C_1$-$C_6$)-alkyl]$_2$, S—($C_1$-$C_6$)-alkyl, S—($CH_2$)$_n$-aryl, S—($CH_2$)$_n$-heterocyclyl, SO—($C_1$-$C_6$)-alkyl, SO—($CH_2$)$_n$-aryl, SO—($CH_2$)$_n$-heterocyclyl, $SO_2$—($C_1$-$C_6$)-alkyl, $SO_2$—($CH_2$)$_n$-aryl, $SO_2$—($CH_2$)$_n$-heterocyclyl, $SO_2$—NH($CH_2$)$_n$-aryl, $SO_2$—NH($CH_2$)$_n$-heterocyclyl, $SO_2$—N(($C_1$-$C_6$)-alkyl)($CH_2$)$_n$-aryl, $SO_2$—N(($C_1$-$C_6$)-alkyl)($CH_2$)$_n$-heterocyclyl, $SO_2$—N(($CH_2$)$_n$-aryl)$_2$, $SO_2$—N(($CH_2$)$_n$-(heterocyclyl))$_2$ where n=0-6 and the aryl radical or heterocyclic radical may be substituted up to two times by F, Cl, Br, OH, $CF_3$, $SF_5$, $NO_2$, CN, $OCF_3$, O—($C_1$-$C_6$)-alkyl, ($C_1$-$C_6$)-alkyl, $NH_2$;

C(NH)($NH_2$), $NH_2$, NH—($C_1$-$C_6$)-alkyl, N(($C_1$-$C_6$)-alkyl)$_2$, NH($C_1$-$C_7$)-acyl, NH—CO—($C_1$-$C_6$)-alkyl, NH—COO—($C_1$-$C_6$)-alkyl, NH—CO-aryl, NH—CO-heterocyclyl, NH—COO-aryl, NH—COO-heterocyclyl, NH—CO—NH—($C_1$-$C_6$)-alkyl), NH—CO—NH-aryl, NH—CO—NH-heterocyclyl, N[($C_1$-$C_6$)-alkyl]-CO—($C_1$-$C_6$)-alkyl, N[($C_1$-$C_6$)-alkyl]-COO—($C_1$-$C_6$)-alkyl, N[($C_1$-$C_6$)-alkyl]-CO-aryl, N[($C_1$-$C_6$)-alkyl]-CO-heterocyclyl, N[($C_1$-$C_6$)-alkyl]-COO-aryl, N[($C_1$-$C_6$)-alkyl]-COO-heterocyclyl, N[($C_1$-$C_6$)-alkyl]-CO—NH—($C_1$-$C_6$)-alkyl), N[($C_1$-$C_6$)-alkyl]-CO—NH-aryl, N[($C_1$-$C_6$)-alkyl]-CO—NH-heterocyclyl, N[($C_1$-$C_6$)-alkyl]-CO—N(($C_1$-$C_6$)-alkyl)$_2$, N[($C_1$-$C_6$)-alkyl]-CO—N(($C_1$-$C_6$)-alkyl)-aryl, N[($C_1$-$C_6$)-alkyl]-CO—N(($C_1$-$C_6$)-alkyl)-heterocyclyl, N[($C_1$-$C_6$)-alkyl]-CO—N(aryl)$_2$, N[($C_1$-$C_6$)-alkyl]-CO—N(heterocyclyl)$_2$, N(aryl)-CO—($C_1$-$C_6$)-alkyl, N(heterocyclyl)-CO—($C_1$-$C_6$)-alkyl, N(aryl)-COO—($C_1$-$C_6$)-alkyl, N(heterocyclyl)-COO—($C_1$-$C_6$)-alkyl, N(aryl)-CO-aryl, N(heterocyclyl)-CO-aryl, N(aryl)-COO-aryl, N(heterocyclyl)-COO-aryl, N(aryl)-CO—NH—($C_1$-$C_6$)-alkyl, N(heterocyclyl)-CO—NH—($C_1$-$C_6$)-alkyl, N(aryl)-CO—NH-aryl, N(heterocyclyl)-CO—NH-aryl, N(aryl)-CO—N(($C_1$-$C_6$)-alkyl)$_2$, N(heterocyclyl)-CO—N(($C_1$-$C_6$)-alkyl)$_2$, N(aryl)-CO—N[($C_1$-$C_6$)-alkyl]-aryl, N(heterocyclyl)-CO—N[($C_1$-$C_6$)-alkyl]-aryl, N(aryl)-CO—N(aryl)$_2$, N(heterocyclyl)-CO—N(aryl)$_2$, aryl, O—($CH_2$)$_n$-aryl, O—($CH_2$)$_n$-heterocyclyl, where n=0-6, where the aryl or heterocyclyl radical may be mono- to trisubstituted by F, Cl, Br, I, OH, $CF_3$, $NO_2$, CN, $OCF_3$, O—($C_1$-$C_6$)-alkyl, ($C_1$-$C_6$)-alkyl, $NH_2$, $NH(C_1$-$C_6)$-alkyl, $N((C_1$-$C_6)$-alkyl)$_2$, $SF_5$, $SO_2$—$CH_3$, COOH, COO—($C_1$-$C_6$)-alkyl, $CONH_2$;

or R1 and R2 together form a 3- to 8-membered aryl, cycloalkyl or heterocyclyl ring, where the aryl, cycloalkyl or heterocyclyl ring may be substituted by F, Cl, Br, I, OH, $CF_3$, $NO_2$, CN, $OCF_3$, O—($C_1$-$C_6$)-alkyl, ($C_1$-$C_6$)-alkyl, $NH_2$, $NH(C_1$-$C_6)$-alkyl, $N((C_1$-$C_6)$-alkyl)$_2$, $SF_5$, $SO_2$—$CH_3$, COOH, COO—($C_1$-$C_6$)-alkyl, $CONH_2$;

and physiologically acceptable salts thereof.

Particular preference is given to using the compounds of the formula I in which

R1 is H, OH, COOH, ($C_1$-$C_8$)-alkyl, ($C_2$-$C_8$)-alkenyl, aryl, where in the ($C_1$-$C_8$)-alkyl and ($C_2$-$C_8$)-alkenyl radicals one or more individual —$CH_2$— or —CH— groups may be replaced by —O— and where the alkyl, alkenyl and aryl radicals may be mono- or polysubstituted by =O, aryl, where the aryl radical may be mono- to trisubstituted by F, Cl, Br, I, OH, $CF_3$, $NO_2$, CN, $OCF_3$, O—($C_1$-$C_6$)-alkyl, $NH_2$, $NH(C_1$-$C_6)$-alkyl, $N((C_1$-$C_6)$-alkyl)$_2$, $SF_5$, $SO_2$—$CH_3$, COOH, COO—($C_1$-$C_6$)-alkyl, $CONH_2$, R2 is H, ($C_1$-$C_8$)-alkyl, ($C_2$-$C_8$)-alkenyl;

and physiologically acceptable salts thereof.

Very particular preference is given to using the compounds of the formula I in which R1 is H, OH, ($C_1$-$C_8$)-alkyl, ($C_2$-$C_4$)-alkenyl, where in the ($C_1$-$C_8$)-alkyl and ($C_2$-$C_4$)-alkenyl radicals one or more individual —$CH_2$— or CH— groups may be replaced by —O— and where the alkyl and alkenyl radicals may be mono- or polysubstituted by =O, aryl, where the aryl radical may be mono- to trisubstituted by F, Cl, Br, I, OH, $CF_3$, $NO_2$, CN, $OCF_3$, O—($C_1$-$C_6$)-alkyl, ($C_1$-$C_6$)-alkyl, $NH_2$, $NH(C_1$-$C_6)$-alkyl, $N((C_1$-$C_6)$-alkyl)$_2$, $SF_5$, $SO_2$—$CH_3$, COOH, COO—($C_1$-$C_6$)-alkyl, $CONH_2$, R2 is H, ($C_1$-$C_8$)-alkyl, ($C_2$-$C_4$)-alkenyl;

and physiologically acceptable salts thereof.

Preference is furthermore given to using the compounds of the formula I in which R1 is ($C_1$-$C_8$)-alkyl or ($C_2$-$C_4$)-alkenyl, where in the ($C_1$-$C_8$)-alkyl and ($C_2$-$C_4$)-alkenyl radicals one or more individual —$CH_2$— or CH— groups may be replaced by —O— and where the alkyl and alkenyl radicals may be mono- or polysubstituted by =O, aryl, where the aryl radical may be mono- to trisubstituted by F, Cl, Br, I, OH, $CF_3$, $NO_2$, CN, $OCF_3$, O—($C_1$-$C_6$)-alkyl, ($C_1$-$C_6$)-alkyl, $NH_2$, $NH(C_1$-$C_6)$-alkyl, $N((C_1$-$C_6)$-alkyl)$_2$, $SF_5$, $SO_2$—$CH_3$, COOH, COO—($C_1$-$C_6$)-alkyl, $CONH_2$, R2 is H, ($C_1$-$C_8$)-alkyl, ($C_2$-$C_4$)-alkenyl;

and physiologically acceptable salts thereof.

Preference is furthermore given to using the compounds of the formula I in which R1 is ($C_2$-$C_8$)-alkyl, where the alkyl radical is mono- or polysubstituted by F;

R2 is H, ($C_1$-$C_8$)-alkyl, ($C_2$-$C_4$)-alkenyl;

and physiologically acceptable salts thereof.

Preference is furthermore given to using the compounds of the formula I in which R1 is H, OH, COOH, ($C_1$-$C_8$)-alkyl, ($C_2$-$C_8$)-alkenyl, aryl, where in the ($C_1$-$C_8$)-alkyl and ($C_2$-$C_8$)-alkenyl radicals one or more individual —$CH_2$— or —CH— groups may be replaced by —O— and where the alkyl, alkenyl and aryl radicals may be mono- or polysubstituted by F, =O, aryl, where the aryl radical may be mono- to trisubstituted by F, Cl, Br, I, OH, $CF_3$, $NO_2$, CN, $OCF_3$, O—($C_1$-$C_6$)-alkyl, ($C_1$-$C_6$)-alkyl, $NH_2$, $NH(C_1$-$C_6)$-alkyl, $N((C_1$-$C_6)$-alkyl)$_2$, $SF_5$, $SO_2$—$CH_3$, COOH, COO—($C_1$-$C_6$)-alkyl, $CONH_2$, R2 is H, ($C_1$-$C_8$)-alkyl, ($C_2$-$C_8$)-alkenyl;

and physiologically acceptable salts thereof, for producing a medicament for the treatment of the metabolic syndrome.

Preference is furthermore given to using the compounds of the formula I in which R1 is H, OH, ($C_1$-$C_8$)-alkyl, ($C_2$-$C_4$)-alkenyl, where in the ($C_1$-$C_8$)-alkyl and ($C_2$-$C_4$)-alkenyl radicals one or more individual —$CH_2$— or —CH— groups may be replaced by —O— and where the alkyl and alkenyl radicals may be mono- or polysubstituted by F, =O, aryl, where the aryl radical may be mono- to trisubstituted by F, Cl, Br, I, OH, $CF_3$, $NO_2$, CN, $OCF_3$, O—($C_1$-$C_6$)-alkyl, ($C_1$-$C_6$)-alkyl, $NH_2$, $NH(C_1$-$C_6)$-alkyl, $N((C_1$-$C_6)$-alkyl)$_2$, $SF_5$, $SO_2$—$CH_3$, COOH, COO—($C_1$-$C_6$)-alkyl, $CONH_2$, R2 is H, ($C_1$-$C_8$)-alkyl, ($C_2$-$C_4$)-alkenyl;

and physiologically acceptable salts thereof, for producing a medicament for the treatment of the metabolic syndrome.

The invention furthermore relates to novel compounds of the formula I

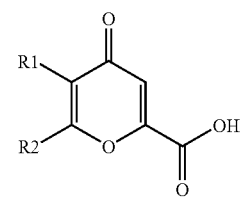

in which

R1 is ($C_1$-$C_8$)-alkyl, ($C_2$-$C_4$)-alkenyl, where in the ($C_1$-$C_8$)-alkyl and ($C_2$-$C_4$)-alkenyl radicals one or more individual —$CH_2$— or —CH— groups may be replaced by —O— and where the alkyl and alkenyl radicals may be mono- or polysubstituted by F;

R2 is H;

and physiologically acceptable salts thereof.

Preference is given to compounds of the formula I in which

R1 is ($C_1$-$C_8$)-alkyl, ($C_2$-$C_4$)-alkenyl, where the alkyl and alkenyl radicals may be mono- or polysubstituted by F;

R2 is H;

and physiologically acceptable salts thereof.

Particular preference is given to compounds of the formula I in which

R1 is ($C_2$-$C_8$)-alkyl, where the alkyl radical may be mono- or polysubstituted by F;

R2 is H;

and physiologically acceptable salts thereof.

Very particular preference is given to compounds of the formula I in which
R1 is $(C_1-C_8)$-alkyl, $(C_2-C_4)$-alkenyl, where in the $(C_1-C_8)$-alkyl and $(C_2-C_4)$-alkenyl radicals one or more individual —$CH_2$— or —CH— groups may be replaced by —O— and where the alkyl and alkenyl radicals are mono- or polysubstituted by F;
R2 is H;
and physiologically acceptable salts thereof.

Very particular preference is furthermore given to compounds of the formula I in which
R1 is $(C_2-C_8)$-alkyl, where the alkyl radical is mono- or polysubstituted by F;
R2 is H;
and physiologically acceptable salts thereof.

In one embodiment, preference is given to compounds of the formula I in which R1 is $(C_2-C_8)$-alkyl, where the alkyl radical may be mono- or polysubstituted by F.

In one embodiment, preference is given to compounds of the formula I in which R1 is $(C_2-C_8)$-alkyl.

In one embodiment, preference is given to compounds of the formula I in which R1 is O—$(C_2-C_8)$-alkyl, where the alkyl radical may be mono- or polysubstituted by F.

In one embodiment, preference is given to compounds of the formula I in which R1 is $(C_2-C_4)$-alkenyl.

In one embodiment, preference is given to compounds of the formula I in which R1 is $(C_2-C_4)$-alkenyl-phenyl, where the phenyl radical may be substituted by F, Cl, Br, I, $CF_3$, $OCF_3$, $NO_2$, $N_3$, CN, $(C_1-C_6)$-alkyl or $O(C_1-C_6)$-alkyl.

In one embodiment, preference is given to compounds of the formula I in which R1 is O-benzyl, where the benzyl radical may be substituted by F, Cl, Br, I, $CF_3$, $OCF_3$, $NO_2$, $N_3$, CN, $(C_1-C_6)$-alkyl or $O(C_1-C_6)$-alkyl.

In one embodiment, preference is given to compounds of the formula I in which R1 is O-phenyl, where the phenyl radical may be substituted by F, Cl, Br, I, $CF_3$, $OCF_3$, $NO_2$, $N_3$, CN, $(C_1-C_6)$-alkyl or $O(C_1-C_6)$-alkyl.

In one embodiment, preference is given to compounds of the formula I in which R1 is phenyl, where the phenyl radical may be substituted by F, Cl, Br, I, $CF_3$, $OCF_3$, $NO_2$, $N_3$, CN, $(C_1-C_6)$-alkyl or $O(C_1-C_6)$-alkyl.

In one embodiment, preference is given to compounds of the formula I in which R2 is H.

In one embodiment, preference is given to compounds of the formula I in which R2 is $(C_1-C_8)$-alkyl.

In one embodiment, preference is given to compounds of the formula I in which R2 is $(C_2-C_4)$-alkenyl.

If radicals or substituents may occur more than once in the compounds of the formula I, then they may all independently of one another have the stated meanings and be identical or different.

The invention relates to the use of the compounds of the formula I in the form of their racemates, racemic mixtures and pure enantiomers, and to their diastereomers and mixtures thereof.

The invention furthermore relates to the use of the compound of the formula I in which R1 and R2 are hydrogen as medicaments.

An alkyl radical means a straight-chain or branched hydrocarbon chain having one or more carbon atoms, such as, for example, methyl, ethyl, propyl, butyl, hexyl, isopropyl, isobutyl, neopentyl, tert-butyl, hexyl.

The alkyl radicals may be substituted one or more times by suitable groups such as, for example: F, Cl, Br, I, $CF_3$, $NO_2$, $N_3$, CN, COOH, COO$(C_1-C_6)$alkyl, $CONH_2$, CONH$(C_1-C_6)$alkyl, CON[$(C_1-C_6)$alkyl]$_2$, cycloalkyl, $(C_2-C_6)$-alkenyl, $(C_2-C_6)$-alkynyl, aryl, heterocyclyl, O—$(C_1-C_6)$-alkyl, O—COO—$(C_1-C_6)$-alkyl, O—CO—$(C_1-C_6)$-alkyl, O—CO—$(C_1-C_6)$-aryl, O—CO—$(C_1-C_6)$-heterocyclyl, $PO_3H_2$, P(O)(Oalkyl)2, $(C_1-C_6)$-alkylene-P(O)(Oalkyl)2, O—P(O)(OH)$_2$, O—P(O)(Oalkyl)$_2$, $SO_3H$, $SO_2$—$NH_2$, $SO_2NH(C_1-C_6)$-alkyl, $SO_2N[(C_1-C_6)$-alkyl]$_2$, S—$(C_1-C_6)$-alkyl, S—$(CH_2)_n$-aryl, S—$(CH_2)_n$-heterocyclyl, SO—$(C_1-C_6)$-alkyl, SO—$(CH_2)_n$-aryl, SO—$(CH_2)_n$-heterocyclyl, $SO_2$—$(C_1-C_6)$-alkyl, $SO_2$—$(CH_2)_n$-aryl, $SO_2$—$(CH_2)_n$-heterocyclyl, $SO_2$—$NH(CH_2)_n$-aryl, $SO_2$—$NH(CH_2)_n$-heterocyclyl, $SO_2$—N[(($C_1-C_6$)-alkyl)($CH_2)_n$-aryl], $SO_2$—N[(($C_1-C_6$)-alkyl)($CH_2)_n$-heterocyclyl], $SO_2$—N(($CH_2)_n$-aryl)$_2$, $SO_2$—N(($CH_2)_n$-(heterocyclyl))$_2$, where n may be 0-6 and the aryl or heterocyclyl radical may be substituted up to three times by F, Cl, Br, OH, $CF_3$, $SF_5$, $NO_2$, CN, $OCF_3$, O—$(C_1-C_6)$-alkyl, $(C_1-C_6)$-alkyl, $NH_2$; C(NH)($NH_2$), $NH_2$, NH—$(C_1-C_6)$-alkyl, N(($C_1-C_6$)-alkyl)$_2$, NH($C_1-C_7$)-acyl, NH—CO—$(C_1-C_6)$-alkyl, NH—COO—$(C_1-C_6)$-alkyl, NH—CO-aryl, NH—CO-heterocyclyl, NH—COO-aryl, NH—COO-heterocyclyl, NH—CO—NH—$(C_1-C_6)$-alkyl), NH—CO—NH-aryl, NH—CO—NH-heterocyclyl, N[($C_1$-$C_6$)-alkyl]-CO—$(C_1-C_6)$-alkyl, N[($C_1-C_6$)-alkyl]-COO—$(C_1-C_6)$-alkyl, N[($C_1-C_6$)-alkyl]-CO-aryl, N[($C_1-C_6$)-alkyl]-CO-heterocyclyl, N[($C_1-C_6$)-alkyl]-COO-aryl, N[($C_1-C_6$)-alkyl]-COO-heterocyclyl, N[($C_1-C_6$)-alkyl]-CO—NH—($C_1-C_6$)-alkyl), N[($C_1-C_6$)-alkyl]-CO—NH-aryl, N[($C_1-C_6$)-alkyl]-CO—NH-heterocyclyl, N[($C_1-C_6$)-alkyl]-CO—N(($C_1-C_6$)-alkyl)$_2$, N[($C_1-C_6$)-alkyl]-CO—N(($C_1-C_6$)-alkyl)aryl, N[($C_1-C_6$)-alkyl]-CO—N(($C_1-C_6$)-alkyl)-heterocyclyl, N[($C_1-C_6$)-alkyl]-CO—N(aryl)$_2$, N[($C_1-C_6$)-alkyl]-CO—N(heterocyclyl)$_2$, N(aryl)-CO—$(C_1-C_6)$-alkyl, N(heterocyclyl)-CO—$(C_1-C_6)$-alkyl, N(aryl)-COO—$(C_1-C_6)$-alkyl, N(heterocyclyl)-COO—$(C_1-C_6)$-alkyl, N(aryl)-CO-aryl, N(heterocyclyl)-CO-aryl, N(aryl)-COO-aryl, N(heterocyclyl)-COO-aryl, N(aryl)-CO—NH—$(C_1-C_6)$-alkyl, N(heterocyclyl)-CO—NH—$(C_1-C_6)$-alkyl, N(aryl)-CO—NH-aryl, N(heterocyclyl)-CO—NH-aryl, N(aryl)-CO—N(($C_1-C_6$)-alkyl)$_2$, N(heterocyclyl)-CO—N(($C_1-C_6$)-alkyl)$_2$, N(aryl)-CO—N[($C_1-C_6$)-alkyl]-aryl, N(heterocyclyl)-CO—N[($C_1-C_6$)-alkyl]-aryl, N(aryl)-CO—N(aryl)$_2$, N(heterocyclyl)-CO—N(aryl)$_2$, aryl, O—$(CH_2)_n$-aryl, O—$(CH_2)_n$-heterocyclyl, where n may be 0-6, where the aryl or heterocyclyl radical may be substituted one to 3 times by F, Cl, Br, I, OH, $CF_3$, $NO_2$, CN, $OCF_3$, O—$(C_1-C_6)$-alkyl, $(C_1-C_6)$-alkyl, $NH_2$, NH($C_1-C_6$)-alkyl, N(($C_1-C_6$)-alkyl)$_2$, $SF_5$, $SO_2$—$CH_3$, COOH, COO—$(C_1-C_6)$-alkyl, $CONH_2$.

An alkenyl radical means a straight-chain or branched hydrocarbon chain having two or more carbon atoms and one or more double bonds, such as, for example, vinyl, allyl, pentenyl.

The alkenyl radicals may be substituted one or more times by suitable groups such as, for example: F, Cl, Br, I, $CF_3$, $NO_2$, $N_3$, CN, COOH, COO$(C_1-C_6)$alkyl, $CONH_2$, CONH$(C_1-C_6)$alkyl, CON[$(C_1-C_6)$alkyl]$_2$, cycloalkyl, $(C_1-C_{10})$-alkyl, $(C_2-C_6)$-alkynyl, aryl, heterocyclyl, O—$(C_1-C_6)$-alkyl O—CO—$(C_1-C_6)$-alkyl, O—CO—$(C_1-C_6)$-aryl, O—CO—$(C_1-C_6)$-heterocyclyl;
$PO_3H_2$, P(O)(Oalkyl)$_2$, $(C_1-C_6)$-alkylene-P(O)(Oalkyl)$_2$, O—P(O)(OH)$_2$, O—P(O)(Oalkyl)$_2$, $SO_3H$, $SO_2$—$NH_2$, $SO_2NH(C_1-C_6)$-alkyl, $SO_2N[(C_1-C_6)$-alkyl]$_2$, S—$(C_1-C_6)$-alkyl, S—$(CH_2)_n$-aryl, S—$(CH_2)_n$-heterocyclyl, SO—$(C_1-C_6)$-alkyl, SO—$(CH_2)_n$-aryl, SO—$(CH_2)_n$-heterocyclyl, $SO_2$—$(C_1-C_6)$-alkyl, $SO_2$—$(CH_2)_n$-aryl, $SO_2$—$(CH_2)_n$-heterocyclyl, $SO_2$—$NH(CH_2)_n$-aryl, $SO_2$—$NH(CH_2)_n$-heterocyclyl, $SO_2$—N(($C_1-C_6$)-alkyl)($CH_2)_n$-aryl, $SO_2$—N(($C_1-C_6$)-alkyl)($CH_2)_n$-heterocyclyl, $SO_2$—N(($CH_2)_n$-aryl)$_2$, $SO_2$—N(($CH_2)_n$-(heterocyclyl)$_2$ where n may be 0-6, and the aryl radical or heterocyclyl radical may be substituted up to twice by F, Cl, Br, OH, $CF_3$, $SF_5$, $NO_2$, CN, $OCF_3$, O—($C_1$-$C_6$)-alkyl, ($C_1$-$C_6$)-alkyl, $NH_2$; $C(NH)(NH_2)$, $NH_2$, NH—($C_1$-$C_6$)-alkyl, $N((C_1$-$C_6$)-alkyl$)_2$, $NH(C_1$-$C_7)$-acyl, NH—CO—($C_1$-$C_6$)-alkyl, NH—COO—($C_1$-$C_6$)-alkyl, NH—CO-aryl, NH—CO-heterocyclyl, NH—COO-aryl, NH—COO-heterocyclyl, NH—CO—NH—($C_1$-$C_6$)-alkyl), NH—CO—NH-aryl, NH—CO—NH-heterocyclyl, N[($C_1$-$C_6$)-alkyl]-CO—($C_1$-$C_6$)-alkyl, N[($C_1$-$C_6$)-alkyl]-COO—($C_1$-$C_6$)-alkyl, N[($C_1$-$C_6$)-alkyl]-CO-aryl, N[($C_1$-$C_6$)-alkyl]-CO-heterocyclyl, N[($C_1$-$C_6$)-alkyl]-COO-aryl, N[($C_1$-$C_6$)-alkyl]-COO-heterocyclyl, N[($C_1$-$C_6$)-alkyl]-CO—NH—($C_1$-$C_6$)-alkyl), N[($C_1$-$C_6$)-alkyl]-CO—NH-aryl, N[($C_1$-$C_6$)-alkyl]-CO—NH-heterocyclyl, N[($C_1$-$C_6$)-alkyl]-CO—N(($C_1$-$C_6$)-alkyl$)_2$, N[($C_1$-$C_6$)-alkyl]-CO—N(($C_1$-$C_6$)-alkyl) aryl, N[($C_1$-$C_6$)-alkyl]-CO—N(($C_1$-$C_6$)-alkyl)-heterocyclyl, N[($C_1$-$C_6$)-alkyl]-CO—N(aryl$)_2$, N[($C_1$-$C_6$)-alkyl]-CO—N(heterocyclyl$)_2$, N(aryl)-CO—($C_1$-$C_6$)-alkyl, N(heterocyclyl)-CO—($C_1$-$C_6$)-alkyl, N(aryl)-COO—($C_1$-$C_6$)-alkyl, N(heterocyclyl)-COO—($C_1$-$C_6$)-alkyl, N(aryl)-CO-aryl, N(heterocyclyl)-CO-aryl, N(aryl)-COO-aryl, N(heterocyclyl)-COO-aryl, N(aryl)-CO—NH—($C_1$-$C_6$)-alkyl, N(heterocyclyl)-CO—NH—($C_1$-$C_6$)-alkyl, N(aryl)-CO—NH-aryl, N(heterocyclyl)-CO—NH-aryl, N(aryl)-CO—N(($C_1$-$C_6$)-alkyl$)_2$, N(heterocyclyl)-CO—N(($C_1$-$C_6$)-alkyl$)_2$, N(aryl)-CO—N[($C_1$-$C_6$)-alkyl]-aryl, N(heterocyclyl)-CO—N[($C_1$-$C_6$)-alkyl]-aryl, N(aryl)-CO—N(aryl$)_2$, N(heterocyclyl)-CO—N(aryl$)_2$, aryl, O—$(CH_2)_n$-aryl, O—$(CH_2)_n$-heterocyclyl, where n may be 0-6, where the aryl or heterocyclyl radical may be substituted one to 3 times by F, Cl, Br, I, OH, $CF_3$, $NO_2$, CN, $OCF_3$, O—($C_1$-$C_6$)-alkyl, ($C_1$-$C_6$)-alkyl, $NH_2$, $NH(C_1$-$C_6$)-alkyl, $N((C_1$-$C_6$)-alkyl$)_2$, $SF_5$, $SO_2$—$CH_3$, COOH, COO—($C_1$-$C_6$)-alkyl, $CONH_2$.

An alkynyl radical means a straight-chain or branched hydrocarbon chain having two or more carbon atoms and one or more triple bonds, such as, for example, ethynyl, propynyl, hexynyl.

The alkynyl radicals may be substituted one or more times by suitable groups such as, for example: F, Cl, Br, I, $CF_3$, $NO_2$, $N_3$, CN, COOH, COO($C_1$-$C_6$)alkyl, $CONH_2$, CONH($C_1$-$C_6$)alkyl, CON[($C_1$-$C_6$)alkyl$]_2$, cycloalkyl, ($C_2$-$C_6$)-alkenyl, ($C_1$-$C_{10}$)-alkyl, O—($C_1$-$C_6$)-alkyl O—CO—($C_1$-$C_6$)-alkyl, 0-CO—($C_1$-$C_6$)-aryl, 0-CO—($C_1$-$C_6$)-heterocyclyl; $PO_3H_2$, $P(O)(Oalkyl)_2$, ($C_1$-$C_6$)-alkylene-$P(O)(Oalkyl)_2$, O—$P(O)(OH)_2$, O—$P(O)(Oalkyl)_2$, $SO_3H$, $SO_2$—$NH_2$, $SO_2NH(C_1$-$C_6$)-alkyl, $SO_2N[(C_1$-$C_6$)-alkyl$]_2$, S—($C_1$-$C_6$)-alkyl, S—$(CH_2)_n$-aryl, S—$(CH_2)_n$-heterocyclyl, SO—($C_1$-$C_6$)-alkyl, SO—$(CH_2)_n$-aryl, SO—$(CH_2)_n$-heterocyclyl, $SO_2$—($C_1$-$C_6$)-alkyl, $SO_2$—$(CH_2)_n$-aryl, $SO_2$—$(CH_2)_n$-heterocyclyl, $SO_2$—$NH(CH_2)_n$-aryl, $SO_2$—$NH(CH_2)_n$-heterocyclyl, $SO_2$—N(($C_1$-$C_6$)-alkyl)$(CH_2)_n$-aryl, $SO_2$—N(($C_1$-$C_6$)-alkyl)$(CH_2)_n$-heterocyclyl, $SO_2$—N(($CH_2)_n$-aryl$)_2$, $SO_2$—N(($CH_2)_n$-(heterocyclyl)$)_2$ where n may be 0-6, and the aryl radical or heterocyclic radical may be substituted up to twice by F, Cl, Br, OH, $CF_3$, $NO_2$, $SF_5$, CN, $OCF_3$, O—($C_1$-$C_6$)-alkyl, ($C_1$-$C_6$)-alkyl, $NH_2$; $C(NH)(NH_2)$, $NH_2$, NH—($C_1$-$C_6$)-alkyl, $N((C_1$-$C_6$)-alkyl$)_2$, $NH(C_1$-$C_7)$-acyl, NH—CO—($C_1$-$C_6$)-alkyl, NH—COO—($C_1$-$C_6$)-alkyl, NH—CO-aryl, NH—CO-heterocyclyl, NH—COO-aryl, NH—COO-heterocyclyl, NH—CO—NH—($C_1$-$C_6$)-alkyl), NH—CO—NH-aryl, NH—CO—NH-heterocyclyl, N[($C_1$-$C_6$)-alkyl]-CO—($C_1$-$C_6$)-alkyl, N[($C_1$-$C_6$)-alkyl]-COO—($C_1$-$C_6$)-alkyl, N[($C_1$-$C_6$)-alkyl]-CO-aryl, N[($C_1$-$C_6$)-alkyl]-CO-heterocyclyl, N[($C_1$-$C_6$)-alkyl]-COO-aryl, N[($C_1$-$C_6$)-alkyl]-COO-heterocyclyl, N[($C_1$-$C_6$)-alkyl]-CO—NH—($C_1$-$C_6$)-alkyl), N[($C_1$-$C_6$)-alkyl]-CO—NH-aryl, N[($C_1$-$C_6$)-alkyl]-CO—NH-heterocyclyl, N[($C_1$-$C_6$)-alkyl]-CO—N(($C_1$-$C_6$)-alkyl$)_2$, N[($C_1$-$C_6$)-alkyl]-CO—N(($C_1$-$C_6$)-alkyl) aryl, N[($C_1$-$C_6$)-alkyl]-CO—N(($C_1$-$C_6$)-alkyl)-heterocyclyl, N[($C_1$-$C_6$)-alkyl]-CO—N(aryl$)_2$, N[($C_1$-$C_6$)-alkyl]-CO—N(heterocyclyl$)_2$, N(aryl)-CO—($C_1$-$C_6$)-alkyl, N(heterocyclyl)-CO—($C_1$-$C_6$)-alkyl, N(aryl)-COO—($C_1$-$C_6$)-alkyl, N(heterocyclyl)-COO—($C_1$-$C_6$)-alkyl, N(aryl)-CO-aryl, N(heterocyclyl)-CO-aryl, N(aryl)-COO-aryl, N(heterocyclyl)-COO-aryl, N(aryl)-CO—NH—($C_1$-$C_6$)-alkyl, N(heterocyclyl)-CO—NH—($C_1$-$C_6$)-alkyl, N(aryl)-CO—NH-aryl, N(heterocyclyl)-CO—NH-aryl, N(aryl)-CO—N(($C_1$-$C_6$)-alkyl$)_2$, N(heterocyclyl)-CO—N(($C_1$-$C_6$)-alkyl$)_2$, N(aryl)-CO—N[($C_1$-$C_6$)-alkyl]-aryl, N(heterocyclyl)-CO—N[($C_1$-$C_6$)-alkyl]-aryl, N(aryl)-CO—N(aryl$)_2$, N(heterocyclyl)-CO—N(aryl$)_2$, aryl, O—$(CH_2)_n$-aryl, O—$(CH_2)_n$-heterocyclyl, where n may be 0-6, where the aryl or heterocyclyl radical may be substituted one to 3 times by F, Cl, Br, I, OH, $CF_3$, $NO_2$, CN, $OCF_3$, O—($C_1$-$C_6$)-alkyl, ($C_1$-$C_6$)-alkyl, $NH_2$, $NH(C_1$-$C_6$)-alkyl, $N((C_1$-$C_6$)-alkyl$)_2$, $SF_5$, $SO_2$—$CH_3$, COOH, COO—($C_1$-$C_6$)-alkyl, $CONH_2$. An aryl radical means a phenyl, naphthyl, biphenyl, tetrahydronaphthyl, alpha- or beta-tetralon-, indanyl or indan-1-onyl radical.

The aryl radicals may be substituted one or more times by suitable groups such as, for example: F, Cl, Br, I, $CF_3$, $NO_2$, $SF_5$, $N_3$, CN, COOH, COO($C_1$-$C_6$)alkyl, $CONH_2$, CONH($C_1$-$C_6$)alkyl, CON[($C_1$-$C_6$)alkyl$]_2$, cycloalkyl, ($C_1$-$C_{10}$)-alkyl, ($C_2$-$C_6$)-alkenyl, ($C_2$-$C_6$)-alkynyl, O—($C_1$-$C_6$)-alkyl O—CO—($C_1$-$C_6$)-alkyl, O—CO—($C_1$-$C_6$)-aryl, O—CO—($C_1$-$C_6$)-heterocyclyl, $PO_3H_2$, $P(O)(Oalkyl)_2$, ($C_1$-$C_6$)-alkylene-$P(O)(Oalkyl)_2$, O—$P(O)(OH)_2$, O—$P(O)(Oalkyl)_2$, $SO_3H$, $SO_2$—$NH_2$, $SO_2NH(C_1$-$C_6$)-alkyl, $SO_2N[(C_1$-$C_6$)-alkyl$]_2$, S—($C_1$-$C_6$)-alkyl, S—$(CH_2)_n$-aryl, S—$(CH_2)_n$-heterocyclyl, SO—($C_1$-$C_6$)-alkyl, SO—$(CH_2)_n$-aryl, SO—$(CH_2)_n$-heterocyclyl, $SO_2$—($C_1$-$C_6$)-alkyl, $SO_2$—$(CH_2)_n$-aryl, $SO_2$—$(CH_2)_n$-heterocyclyl, $SO_2$—$NH(CH_2)_n$-aryl, $SO_2$—$NH(CH_2)_n$-heterocyclyl, $SO_2$—N(($C_1$-$C_6$)-alkyl)$(CH_2)_n$-aryl, $SO_2$—N(($C_1$-$C_6$)-alkyl)$(CH_2)_n$-heterocyclyl, $SO_2$—N(($CH_2)_n$-aryl$)_2$, $SO_2$—N(($CH_2)_n$-(heterocyclyl)$)_2$ where n may be 0-6, and the aryl radical or heterocyclic radical may be substituted up to twice by F, Cl, Br, OH, $CF_3$, $NO_2$, $SF_5$, CN, $OCF_3$, O—($C_1$-$C_6$)-alkyl, ($C_1$-$C_6$)-alkyl, $NH_2$; $C(NH)(NH_2)$, $NH_2$, NH—($C_1$-$C_6$)-alkyl, $N((C_1$-$C_6$)-alkyl$)_2$, $NH(C_1$-$C_7)$-acyl, NH—CO—($C_1$-$C_6$)-alkyl, NH—COO—($C_1$-$C_6$)-alkyl, NH—CO-aryl, NH—CO-heterocyclyl, NH—COO-aryl, NH—COO-heterocyclyl, NH—CO—NH—($C_1$-$C_6$)-alkyl), NH—CO—NH-aryl, NH—CO—NH-heterocyclyl, N[($C_1$-$C_6$)-alkyl]-CO—($C_1$-$C_6$)-alkyl, N[($C_1$-$C_6$)-alkyl]-COO—($C_1$-$C_6$)-alkyl, N[($C_1$-$C_6$)-alkyl]-CO-aryl, N[($C_1$-$C_6$)-alkyl]-CO-heterocyclyl, N[($C_1$-$C_6$)-alkyl]-COO-aryl, N[($C_1$-$C_6$)-alkyl]-COO-heterocyclyl, N[($C_1$-$C_6$)-alkyl]-CO—NH—($C_1$-$C_6$)-alkyl), N[($C_1$-$C_6$)-alkyl]-CO—NH-aryl, N[($C_1$-$C_6$)-alkyl]-CO—NH-heterocyclyl, N[($C_1$-$C_6$)-alkyl]-CO—N(($C_1$-$C_6$)-alkyl$)_2$, N[($C_1$-$C_6$)-alkyl]-CO—N(($C_1$-$C_6$)-alkyl) aryl, N[($C_1$-$C_6$)-alkyl]-CO—N(($C_1$-$C_6$)-alkyl)-heterocyclyl, N[($C_1$-$C_6$)-alkyl]-CO—N(aryl$)_2$, N[($C_1$-$C_6$)-alkyl]-CO—N(heterocyclyl$)_2$, N(aryl)-CO—($C_1$-$C_6$)-alkyl, N(heterocyclyl)-CO—($C_1$-$C_6$)-alkyl, N(aryl)-COO—($C_1$-$C_6$)-alkyl, N(heterocyclyl)-COO—($C_1$-$C_6$)-alkyl, N(aryl)-CO-aryl, N(heterocyclyl)-CO-aryl, N(aryl)-COO-aryl, N(heterocyclyl)-COO-aryl, N(aryl)-CO—NH—($C_1$-$C_6$)-alkyl, N(heterocyclyl)-CO—NH—($C_1$-$C_6$)-alkyl, N(aryl)-CO—NH-aryl, N(heterocyclyl)-CO—NH-aryl, N(aryl)-CO—N(($C_1$-$C_6$)-alkyl$)_2$, N(heterocyclyl)-CO—N(($C_1$-$C_6$)-alkyl$)_2$, N(aryl)-CO—N[($C_1$-$C_6$)-alkyl]-aryl, N(heterocyclyl)-CO—N[($C_1$-$C_6$)-alkyl]-aryl, N(aryl)-CO—N(aryl$)_2$, N(heterocyclyl)-CO—N(aryl$)_2$, aryl, O—$(CH_2)_n$-aryl, O—$(CH_2)_n$-heterocyclyl, where n may be 0-6, where the aryl or heterocyclyl radical may be substituted one to 3 times by F, Cl, Br, I, OH, CF$_3$, NO$_2$, CN, OCF$_3$, O—(C$_1$-C$_6$)-alkyl, (C$_1$-C$_6$)-alkyl, NH$_2$, NH(C$_1$-C$_6$)-alkyl, N((C$_1$-C$_6$)-alkyl)$_2$, SF$_5$, SO$_2$—CH$_3$, COOH, COO—(C$_1$-C$_6$)-alkyl, CONH$_2$.

A cycloalkyl radical means a ring system which comprises one or more rings and which is in saturated or partially unsaturated (having one or two double bonds) form, which is composed exclusively of carbon atoms, such as, for example, cyclopropyl, cyclopentyl, cyclopentenyl, cyclohexyl or adamantyl.

The cycloalkyl radicals may be substituted one or more times by suitable groups such as, for example: F, Cl, Br, I, CF$_3$, NO$_2$, N$_3$, CN, COOH, COO(C$_1$-C$_6$)alkyl, CONH$_2$, CONH(C$_1$-C$_6$)alkyl, CON[(C$_1$-C$_6$)alkyl]$_2$, cycloalkyl, (C$_1$-C$_{10}$)-alkyl, (C$_2$-C$_6$)-alkenyl, (C$_2$-C$_6$)-alkynyl, O—(C$_1$-C$_6$)-alkyl O—CO—(C$_1$-C$_6$)-alkyl, O—CO—(C$_1$-C$_6$)-aryl, O—CO—(C$_1$-C$_6$)-heterocyclyl;
PO$_3$H$_2$, P(O)(Oalkyl)$_2$, (C$_1$-C$_6$)-alkylene-P(O)(Oalkyl)$_2$, O—P(O)(OH)$_2$, O—P(O)(Oalkyl)$_2$, SO$_3$H, SO$_2$—NH$_2$, SO$_2$NH(C$_1$-C$_6$)-alkyl, SO$_2$N[(C$_1$-C$_6$)-alkyl]$_2$, S—(C$_1$-C$_6$)-alkyl, S—(CH$_2$)$_n$-aryl, S—(CH$_2$)$_n$-heterocyclyl, SO—(C$_1$-C$_6$)-alkyl, SO—(CH$_2$)$_n$-aryl, SO—(CH$_2$)$_n$-heterocyclyl, SO$_2$—(C$_1$-C$_6$)-alkyl, SO$_2$—(CH$_2$)$_n$-aryl, SO$_2$—(CH$_2$)$_n$-heterocyclyl, SO$_2$—NH(CH$_2$)$_n$-aryl, SO$_2$—NH(CH$_2$)$_n$-heterocyclyl, SO$_2$—N((C$_1$-C$_6$)-alkyl)(CH$_2$)$_n$-aryl, SO$_2$—N((C$_1$-C$_6$)-alkyl)(CH$_2$)$_n$-heterocyclyl, SO$_2$—N((CH$_2$)$_n$-aryl)$_2$, SO$_2$—N((CH$_2$)$_n$-(heterocyclyl))$_2$ where n may be 0-6, and the aryl radical or heterocyclic radical may be substituted up to twice by F, Cl, Br, OH, CF$_3$, SF$_5$, NO$_2$, CN, OCF$_3$, O—(C$_1$-C$_6$)-alkyl, (C$_1$-C$_6$)-alkyl, NH$_2$; C(NH)(NH$_2$), NH$_2$, NH—(C$_1$-C$_6$)-alkyl, N((C$_1$-C$_6$)-alkyl)$_2$, NH(C$_1$-C$_7$)-acyl, NH—CO—(C$_1$-C$_6$)-alkyl, NH—COO—(C$_1$-C$_6$)-alkyl, NH—CO-aryl, NH—CO-heterocyclyl, NH—COO-aryl, NH—COO-heterocyclyl, NH—CO—NH—(C$_1$-C$_6$)-alkyl), NH—CO—NH-aryl, NH—CO—NH-heterocyclyl, N[(C$_1$-C$_6$)-alkyl]-CO—(C$_1$-C$_6$)-alkyl, N[(C$_1$-C$_6$)-alkyl]-COO—(C$_1$-C$_6$)-alkyl, N[(C$_1$-C$_6$)-alkyl]-CO-aryl, N[(C$_1$-C$_6$)-alkyl]-CO-heterocyclyl, N[(C$_1$-C$_6$)-alkyl]-COO-aryl, N[(C$_1$-C$_6$)-alkyl]-COO-heterocyclyl, N[(C$_1$-C$_6$)-alkyl]-CO—NH—(C$_1$-C$_6$)-alkyl), N[(C$_1$-C$_6$)-alkyl]-CO—NH-aryl, N[(C$_1$-C$_6$)-alkyl]-CO—NH-heterocyclyl, N[(C$_1$-C$_6$)-alkyl]-CO—N((C$_1$-C$_6$)-alkyl)$_2$, N[(C$_1$-C$_6$)-alkyl]-CO—N((C$_1$-C$_6$)-alkyl)aryl, N[(C$_1$-C$_6$)-alkyl]-CO—N((C$_1$-C$_6$)-alkyl)-heterocyclyl, N[(C$_1$-C$_6$)-alkyl]-CO—N(aryl)$_2$, N[(C$_1$-C$_6$)-alkyl]-CO—N(heterocyclyl)$_2$, N(aryl)-CO—(C$_1$-C$_6$)-alkyl, N(heterocyclyl)-CO—(C$_1$-C$_6$)-alkyl, N(aryl)-COO—(C$_1$-C$_6$)-alkyl, N(heterocyclyl)-COO—(C$_1$-C$_6$)-alkyl, N(aryl)-CO-aryl, N(heterocyclyl)-CO-aryl, N(aryl)-COO-aryl, N(heterocyclyl)-COO-aryl, N(aryl)-CO—NH—(C$_1$-C$_6$)-alkyl, N(heterocyclyl)-CO—NH—(C$_1$-C$_6$)-alkyl, N(aryl)-CO—NH-aryl, N(heterocyclyl)-CO—NH-aryl, N(aryl)-CO—N((C$_1$-C$_6$)-alkyl)$_2$, N(heterocyclyl)-CO—N((C$_1$-C$_6$)-alkyl)$_2$, N(aryl)-CO—N[(C$_1$-C$_6$)-alkyl]-aryl, N(heterocyclyl)-CO—N[(C$_1$-C$_6$)-alkyl]-aryl, N(aryl)-CO—N(aryl)$_2$, N(heterocyclyl)-CO—N(aryl)$_2$, aryl, O—(CH$_2$)$_n$-aryl, O—(CH$_2$)$_n$-heterocyclyl, where n may be 0-6, where the aryl or heterocyclyl radical may be substituted one to 3 times by F, Cl, Br, I, OH, CF$_3$, NO$_2$, CN, OCF$_3$, O—(C$_1$-C$_6$)-alkyl, (C$_1$-C$_6$)-alkyl, NH$_2$, NH(C$_1$-C$_6$)-alkyl, N((C$_1$-C$_6$)-alkyl)$_2$, SF$_5$, SO$_2$—CH$_3$, COOH, COO—(C$_1$-C$_6$)-alkyl, CONH$_2$.

Heterocycle, heterocyclyl or heterocyclic radical means rings and ring systems which, apart from carbon, also comprise heteroatoms such as, for example, nitrogen, oxygen or sulfur. This definition also includes ring systems in which the heterocycle or the heterocyclic radical is fused to benzene nuclei.

Suitable heterocyclyl or "heterocyclic radicals" are acridinyl, benzimidazolyl, benzofuryl, benzothienyl, benzothiophenyl, benzoxazolyl, benzthiazolyl, benztriazolyl, benzisoxazolyl, benzisothiazolyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, decahydroquinolinyl, 2H,6H-1,5,2-dithiazinyl, dihydrofuro[2,3-b]-tetra-hydrofuran, furyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purynyl, pyranyl, pyrazinyl, pyroazolidinyl, pyrazolinyl, pyrazolyl, pyridazinyl, pyridooxazoles, pyridoimidazoles, pyridothiazol, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, 6H-1,2,5-thiadazinyl, thiazolyl, 1,2,3-thiadiazolyl, 1,2,4-thiadiazolyl, 1,2,5-thiadiazolyl, 1,3,4-thiadiazolyl, thienyl, triazolyl, tetrazolyl, aziridinyl, azetininyl, azepanyl, azocanyl and xanthenyl.

Pyridyl stands both for 2-, 3- and 4-pyridyl. Thienyl stands both for 2- and 3-thienyl. Furyl stands both for 2- and 3-furyl.

Also included are the corresponding N-oxides of these compounds, i.e. for example 1-oxy-2-, 3- or 4-pyridyl.

Also included are derivatives of these heterocycles which are benzo-fused one or more times.

The heterocyclic rings or heterocyclic radicals may be substituted one or more times by suitable groups such as, for example: F, Cl, Br, I, CF$_3$, NO$_2$, N$_3$, CN, COOH, COO(C$_1$-C$_6$)alkyl, CONH$_2$, CONH(C$_1$-C$_6$)alkyl, CON[(C$_1$-C$_6$)alkyl]$_2$, cycloalkyl, (C$_1$-C$_{10}$)-alkyl, (C$_2$-C$_6$)-alkenyl, (C$_2$-C$_6$)-alkynyl, O—(C$_1$-C$_6$)-alkyl O—CO—(C$_1$-C$_6$)-alkyl, O—CO—(C$_1$-C$_6$)-aryl, O—CO—(C$_1$-C$_6$)-heterocyclyl;
PO$_3$H$_2$, P(O)(Oalkyl)$_2$, (C$_1$-C$_6$)-alkylene-P(O)(Oalkyl)$_2$, O—P(O)(OH)$_2$, O—P(O)(Oalkyl)$_2$, SO$_3$H, SO$_2$—NH$_2$, SO$_2$NH(C$_1$-C$_6$)-alkyl, SO$_2$N[(C$_1$-C$_6$)-alkyl]$_2$, S—(C$_1$-C$_6$)-alkyl, S—(CH$_2$)$_n$-aryl, S—(CH$_2$)$_n$-heterocyclyl, SO—(C$_1$-C$_6$)-alkyl, SO—(CH$_2$)$_n$-aryl, SO—(CH$_2$)$_n$-heterocyclyl, SO$_2$—(C$_1$-C$_6$)-alkyl, SO$_2$—(CH$_2$)$_n$-aryl, SO$_2$—(CH$_2$)$_n$-heterocyclyl, SO$_2$—NH(CH$_2$)$_n$-aryl, SO$_2$—NH(CH$_2$)$_n$-heterocyclyl, SO$_2$—N((C$_1$-C$_6$)-alkyl)(CH$_2$)$_n$-aryl, SO$_2$—N(C$_1$-C$_6$)-alkyl)(CH$_2$)$_n$-heterocyclyl, SO$_2$—N((CH$_2$)$_n$-aryl)$_2$, SO$_2$—N((CH$_2$)$_n$-(heterocyclyl))$_2$ where n may be 0-6, and the aryl radical or heterocyclic radical may be substituted up to twice by F, Cl, Br, OH, CF$_3$, SF$_5$, NO$_2$, CN, OCF$_3$, O—(C$_1$-C$_6$)-alkyl, (C$_1$-C$_6$)-alkyl, NH$_2$;
C(NH)(NH$_2$), NH$_2$, NH—(C$_1$-C$_6$)-alkyl, N((C$_1$-C$_6$)-alkyl)$_2$, NH(C$_1$-C$_7$)-acyl, NH—CO—(C$_1$-C$_6$)-alkyl, NH—COO—(C$_1$-C$_6$)-alkyl, NH—CO-aryl, NH—CO-heterocyclyl, NH—COO-aryl, NH—COO-heterocyclyl, NH—CO—NH—(C$_1$-C$_6$)-alkyl), NH—CO—NH-aryl, NH—CO—NH-heterocyclyl, N[(C$_1$-C$_6$)-alkyl]-CO—(C$_1$-C$_6$)-alkyl, N[(C$_1$-C$_6$)-alkyl]-COO—(C$_1$-C$_6$)-alkyl, N[(C$_1$-C$_6$)-alkyl]-CO-aryl, N[(C$_1$-C$_6$)-alkyl]-CO-heterocyclyl, N[(C$_1$-C$_6$)-alkyl]-COO-aryl, N[(C$_1$-C$_6$)-alkyl]-COO-heterocyclyl, N[(C$_1$-C$_6$)-alkyl]-CO—NH—(C$_1$-C$_6$)-alkyl), N[(C$_1$-C$_6$)-alkyl]-CO—NH-aryl, N[(C$_1$-C$_6$)-alkyl]-CO—NH-heterocyclyl, N[(C$_1$-C$_6$)-alkyl]-CO—N((C$_1$-C$_6$)-alkyl)$_2$, N[(C$_1$-C$_6$)-alkyl]-CO—N((C$_1$-C$_6$)-alkyl)-aryl, N[(C$_1$-C$_6$)-alkyl]-CO—N((C$_1$-C$_6$)-alkyl)-heterocyclyl, N[(C$_1$-C$_6$)-alkyl]-CO—N(aryl)$_2$, N[(C$_1$-C$_6$)-alkyl]-CO—N(heterocyclyl)$_2$, N(aryl)-CO—(C$_1$-C$_6$)-alkyl, N(heterocyclyl)-CO—(C$_1$-C$_6$)-alkyl, N(aryl)-COO—(C$_1$-C$_6$)-alkyl, N(heterocyclyl)-COO—(C$_1$-C$_6$)- alkyl, N(aryl)-CO-aryl, N(heterocyclyl)-CO-aryl, N(aryl)-COO-aryl, N(heterocyclyl)-COO-aryl, N(aryl)-CO—NH—$(C_1\text{-}C_6)$-alkyl, N(heterocyclyl)-CO—NH—$(C_1\text{-}C_6)$-alkyl, N(aryl)-CO—NH-aryl, N(heterocyclyl)-CO—NH-aryl, N(aryl)-CO—N$((C_1\text{-}C_6)$-alkyl$)_2$, N(heterocyclyl)-CO—N$((C_1\text{-}C_6)$-alkyl$)_2$, N(aryl)-CO—N$[(C_1\text{-}C_6)$-alkyl]-aryl, N(heterocyclyl)-CO—N$[(C_1\text{-}C_6)$-alkyl]-aryl, N(aryl)-CO—N(aryl)$_2$, N(heterocyclyl)-CO—N(aryl)$_2$, aryl, O—$(CH_2)_n$-aryl, O—$(CH_2)_n$-heterocyclyl, where n may be 0-6, where the aryl or heterocyclyl radical may be substituted one to 3 times by F, Cl, Br, I, OH, $CF_3$, $NO_2$, CN, $OCF_3$, $SF_5$, O—$(C_1\text{-}C_6)$-alkyl, $(C_1\text{-}C_6)$-alkyl, $NH_2$, NH$(C_1\text{-}C_6)$-alkyl, N$((C_1\text{-}C_6)$-alkyl$)_2$, $SF_5$, $SO_2$—$CH_3$, COOH, COO—$(C_1\text{-}C_6)$-alkyl, $CONH_2$.

Pharmaceutically acceptable salts are, because their solubility in water is greater than that of the initial or basic compounds, particularly suitable for medical applications. These salts must have a pharmaceutically acceptable anion or cation. Suitable pharmaceutically acceptable acid addition salts of the compounds of the formula I are salts of inorganic acids such as hydrochloric acid, hydrobromic, phosphoric, metaphosphoric, nitric, sulfonic and sulfuric acids, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic, tartaric and trifluoroacetic acids, also L-ascorbic acid, salicylic acid, 1,2-benzisothiazol-3(2H)-one and 6-methyl-1,2,3-oxathiazin-4(3H)-one 2,2-dioxide. The chlorine salt is particularly preferably used for medical purposes. Suitable pharmaceutically acceptable basic salts are ammonium salts, alkali metal salts (such as sodium and potassium salts) and alkaline earth metal salts (such as magnesium and calcium salts).

Salts with a pharmaceutically unacceptable anion likewise belong within the framework of the invention as useful intermediates for preparing or purifying pharmaceutically acceptable salts and/or for use in nontherapeutic, for example in vitro, applications.

The compounds of the formula I may also exist in various polymorphous forms, for example as amorphous and crystalline polymorphous forms. All polymorphous forms of the compounds of the formula I belong within the framework of the invention and are a further aspect of the invention.

All references to "compound(s) of formula (I)" hereinafter refer to compound(s) of the formula (I) as described above, and their salts and solvates as described herein.

The compound(s) of the formula (I) may also be administered in combination with further active ingredient.

The amount of a compound of formula (I) necessary to achieve the desired biological effect depends on a number of factors, e.g. the specific compound chosen, the intended use, the mode of administration and the clinical condition of the patient. The daily dose is generally in the range from 0.3 mg to 100 mg (typically from 3 mg to 50 mg) per day per kilogram of body weight, e.g. 3-10 mg/kg/day. An intravenous dose may be, for example, in the range from 0.3 mg to 1.0 mg/kg, which can suitably be administered as infusion of 10 ng to 100 ng per kilogram per minute. Suitable infusion solutions for these purposes may comprise for example from 0.1 ng to 10 mg, typically from 1 ng to 10 mg, per milliliter. Single doses may comprise for example from 1 mg to 10 g of the active ingredient. Thus, ampoules for injections may comprise for example from 1 mg to 100 mg, and single-dose formulations which can be administered orally, such as, for example, capsules or tablets, may comprise for example from 1.0 to 1000 mg, typically from 10 to 600 mg. In the case of pharmaceutically acceptable salts, the aforementioned weight data refer to the weight of the benzothiazepine ion derived from the salt. For the prophylaxis or therapy of the abovementioned conditions, the compounds of formula (I) may be used as the compound itself, but they are preferably in the form of a pharmaceutical composition with an acceptable carrier. The carrier must, of course, be acceptable in the sense that it is compatible with the other ingredients of the composition and is not harmful for the patient's health. The carrier may be a solid or a liquid or both and is preferably formulated with the compound as a single dose, for example as a tablet, which may comprise from 0.05% to 95% by weight of the active ingredient. Further pharmaceutically active substances may likewise be present, including further compounds of formula (I). The pharmaceutical compositions of the invention can be produced by one of the known pharmaceutical methods, which essentially consist of mixing the ingredients with pharmacologically acceptable carriers and/or excipients.

Pharmaceutical compositions of the invention are those suitable for oral, rectal, topical, peroral (for example sublingual) and parenteral (e.g. subcutaneous, intramuscular, intradermal or intravenous) administration, although the most suitable mode of administration depends in each individual case on the nature and severity of the condition to be treated and on the nature of the compound of formula (I) used in each case. Coated formulations and coated slow-release formulations also belong within the framework of the invention. Preference is given to acid- and gastric juice-resistant formulations. Suitable gastric juice-resistant coatings include cellulose acetate phthalate, polyvinal acetate phthalate, hydroxypropylmethylcellulose phthalate and anionic polymers of methacrylic acid and methyl methacrylate.

Suitable pharmaceutical compounds for oral administration may be in the form of separate units such as, for example, capsules, cachets, suckable tablets or tablets, each of which contain a defined amount of the compound of formula (I); as powders or granules, as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients.

Compressed tablets can be produced by tableting the compound in free-flowing form such as, for example, a powder or granules, where appropriate mixed with a binder, glidant, inert diluent and/or one (or more) surface-active/dispersing agent(s) in a suitable machine. Molded tablets can be produced by molding the compound, which is in powder form and is moistened with an inert liquid diluent, in a suitable machine.

Pharmaceutical compositions which are suitable for peroral (sublingual) administration comprise suckable tablets which contain a compound of formula (I) with a flavoring, normally sucrose and gum arabic or tragacanth, and pastilles which comprise the compound in an inert base such as gelatin and glycerol or sucrose and gum arabic.

Pharmaceutical compositions suitable for parenteral administration comprise preferably sterile aqueous preparations of a compound of formula (I), which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with the blood. Injectable compositions of the invention generally contain from 0.1 to 5% by weight of the active compound.

Pharmaceutical compositions suitable for rectal administration are preferably in the form of single-dose suppositories. These can be produced by mixing a compound of formula (I) with one or more conventional solid carriers, for example cocoa butter, and shaping the resulting mixture.

Pharmaceutical compositions suitable for topical use on the skin are preferably in the form of ointment, cream, lotion, paste, spray, aerosol or oil. Carriers which can be used are petrolatum, lanolin, polyethylene glycols, alcohols and combinations of two or more of these substances. The active ingredient is generally present in a concentration of from 0.1 to 15% by weight of the composition, for example from 0.5 to 2%.

Transdermal administration is also possible. Pharmaceutical compositions suitable for transdermal uses can be in the form of single plasters which are suitable for long-term close contact with the patient's epidermis. Such plasters suitably contain the active ingredient in an aqueous solution which is buffered where appropriate, dissolved and/or dispersed in an adhesive or dispersed in a polymer. A suitable active ingredient concentration is about 1% to 35%, preferably about 3% to 15%. A particular possibility is for the active ingredient to be released by electrotransport or iontophoresis as described, for example, in Pharmaceutical Research, 2(6): 318 (1986).

Further active ingredients suitable for combination products are:
all antidiabetics mentioned in the Rote Liste 2006, chapter 12. They may be combined with the compounds of the formula I of the invention in particular for a synergistic improvement of the effect. Administration of the active ingredient combination may take place either by separate administration of the active ingredients to the patient or in the form of combination products in which a plurality of active ingredients are present in one pharmaceutical preparation. Most of the active ingredients listed below are disclosed in the USP Dictionary of USAN and International Drug Names, US Pharmacopeia, Rockville 2001.

Antidiabetics include insulin and insulin derivatives such as, for example, Lantus® (see www.lantus.com) or HMR 1964, fast-acting insulins (see U.S. Pat. No. 6,221,633), GLP-1 derivatives such as, for example, those disclosed in WO 98/08871 of Novo Nordisk A/S, and orally effective hypoglycemic active ingredients.

The orally effective hypoglycemic active ingredients include, preferably, sulfonylureas, biguanidines, meglitinides, oxadiazolidinediones, thiazolidinediones, glucosidase inhibitors, glucagon antagonists, GLP-1 agonists, potassium channel openers such as, for example, those disclosed in WO 97/26265 and WO 99/03861 of Novo Nordisk A/S, insulin sensitizers, inhibitors of liver enzymes involved in the stimulation of gluconeogenesis and/or glycogenolysis, modulators of glucose uptake, compounds which alter lipid metabolism, such as antihyperlipidemic active ingredients and antilipidemic active ingredients, compounds which reduce food intake, PPAR and PXR agonists and active ingredients which act on the ATP-dependent potassium channel of the beta cells.

In one embodiment of the invention, the compounds of the formula I are administered in combination with an HMGCoA reductase inhibitor such as simvastatin, fluvastatin, pravastatin, lovastatin, atorvastatin, cerivastatin, rosuvastatin.

In one embodiment of the invention, the compounds of the formula I are administered in combination with a cholesterol absorption inhibitor such as, for example, ezetimibe, tiqueside, pamaqueside, or with a compound as described in PCT/EP 2004/00269, PCT/EP 2003/05815, PCT/EP 2003/05814, PCT/EP 2003/05816, EP 0114531, U.S. Pat. No. 6,498,156.

In one embodiment of the invention, the compounds of the formula I are administered in combination with a PPAR gamma agonist, such as, for example, rosiglitazone, pioglitazone, JTT-501, GI 262570.

In one embodiment of the invention, the compounds of the formula I are administered in combination with a PPAR alpha agonist, such as, for example, GW 9578, GW 7647.

In one embodiment of the invention, the compounds of the formula I are administered in combination with a mixed PPAR alpha/gamma agonist, such as, for example, GW 1536, AVE 8042, AVE 8134, AVE 0847, or as described in PCT/US 2000/11833, PCT/US 2000/11490, WO 03/020269.

In one embodiment of the invention, the compounds of the formula I are administered in combination with a fibrate such as, for example, fenofibrate, clofibrate, bezafibrate.

In one embodiment of the invention, the compounds of the formula I are administered in combination with an MTP inhibitor such as, for example, implitapide, BMS-201038, R-103757.

In one embodiment of the invention, the compounds of the formula I are administered in combination with bile acid absorption inhibitor (see, for example, U.S. Pat. No. 6,245,744 or U.S. Pat. No. 6,221,897), such as, for example, HMR 1741.

In one embodiment of the invention, the compounds of the formula I are administered in combination with a CETP inhibitor, such as, for example, JTT-705.

In one embodiment of the invention, the compounds of the formula I are administered in combination with a polymeric bile acid adsorbent such as, for example, cholestyramine, colesevelam.

In one embodiment of the invention, the compounds of the formula I are administered in combination with an LDL receptor inducer (see U.S. Pat. No. 6,342,512), such as, for example, HMR1171, HMR1586.

In one embodiment of the invention, the compounds of the formula I are administered in combination with an ACAT inhibitor, such as, for example, avasimibe.

In one embodiment of the invention, the compounds of the formula I are administered in combination with an antioxidant, such as, for example, OPC-14117.

In one embodiment of the invention, the compounds of the formula I are administered in combination with a lipoprotein lipase inhibitor, such as, for example, NO-1886.

In one embodiment of the invention, the compounds of the formula I are administered in combination with an ATP-citrate lyase inhibitor, such as, for example, SB-204990.

In one embodiment of the invention, the compounds of the formula I are administered in combination with a squalene synthetase inhibitor, such as, for example, BMS-188494.

In one embodiment of the invention, the compounds of the formula I are administered in combination with a lipoprotein (a) antagonist, such as, for example, CI-1027 or nicotinic acid.

In one embodiment of the invention, the compounds of the formula I are administered in combination with a lipase inhibitor, such as, for example, orlistat.

In one embodiment of the invention, the compounds of the formula I are administered in combination with insulin.

In one embodiment, the compounds of the formula I are administered in combination with a sulfonylurea such as, for example, tolbutamide, glibenclamide, glipizide or glimepiride.

In one embodiment, the compounds of the formula I are administered in combination with a biguanide, such as, for example, metformin.

In one further embodiment, the compounds of the formula I are administered in combination with a meglitinide, such as, for example, repaglinide.

In one embodiment, the compounds of the formula I are administered in combination with a thiazolidinedione, such as, for example, troglitazone, ciglitazone, pioglitazone, rosiglitazone or the compounds disclosed in WO 97/41097 of Dr. Reddy's Research Foundation, in particular 5-[[4-[(3,4-dihydro-3-methyl-4-oxo-2-quinazolinylmethoxy]-phenyl]methyl]-2,4-thiazolidinedione.

In one embodiment, the compounds of the formula I are administered in combination with an α-glucosidase inhibitor, such as, for example, miglitol or acarbose.

In one embodiment, the compounds of the formula I are administered in combination with an adenosine A1 agonist such as, for example, those described in EP 0912520 or PCT/EP06749.

In one embodiment, the compounds of the formula I are administered in combination with an active ingredient which acts on the ATP-dependent potassium channel of the beta cells, such as, for example, tolbutamide, glibenclamide, glipizide, glimepiride or repaglinide.

In one embodiment, the compounds of the formula I are administered in combination with more than one of the aforementioned compounds, e.g. in combination with a sulfonylurea and metformin, with a sulfonylurea and acarbose, repaglinide and metformin, insulin and a sulfonylurea, insulin and metformin, insulin and troglitazone, insulin and lovastatin, etc.

In a further embodiment, the compounds of the formula I are administered in combination with CART modulators (see "Cocaine-amphetamine-regulated transcript influences energy metabolism, anxiety and gastric emptying in mice" Asakawa, A, et al., M.: Hormone and Metabolic Research (2001), 33(9), 554-558), NPY antagonists, e.g. naphthalene-1-sulfonic acid {4-[(4-aminoquinazolin-2-ylamino)methyl]cyclohexylmethyl}amide, hydrochloride (CGP 71683A)), MC4 agonists (e.g. 1-amino-1,2,3,4-tetrahydronaphthalene-2-carboxylic acid [2-(3a-benzyl-2-methyl-3-oxo-2,3,3a,4,6,7-hexahydropyrazolo[4,3-c]pyridin-5-yl)-1-(4-chlorophenyl)-2-oxoethyl]amide; (WO 01/91752)), orexin antagonists (e.g. 1-(2-methylbenzoxazol-6-yl)-3-[1,5]naphthyridin-4-ylurea hydrochloride (SB-334867-A)), H3 agonists (3-cyclohexyl-1-(4,4-dimethyl-1,4,6,7-tetrahydroimidazo[4,5-c]pyridin-5-yl)propan-1-one oxalic acid salt (WO 00/63208)); TNF agonists, CRF antagonists (e.g. [2-methyl-9-(2,4,6-trimethylphenyl)-9H-1,3,9-triazafluoren-4-yl]dipropylamine (WO 00/66585)), CRF BP antagonists (e.g. urocortin), urocortin agonists, β3 agonists (e.g. 1-(4-chloro-3-methanesulfonylmethylphenyl)-2-[2-(2,3-dimethyl-1H-indol-6-yloxy)ethyl-amino]ethanol hydrochloride (WO 01/83451)), CB1 (cannabinoid receptor 1) receptor antagonists (e.g. rimonabant or the active ingredients mentioned in WO 02/28346, MSH (melanocyte-stimulating hormone) agonists, CCK-A agonists (e.g. {2-[4-(4-chloro-2,5-dimethoxyphenyl)-5-(2-cyclohexylethyl)thiazol-2-ylcarbamoyl]-5,7-dimethylindol-1-yl}acetic acid trifluoroacetic acid salt (WO 99/15525)), serotonin reuptake inhibitors (e.g. dexfenfluramine), mixed serotoninergic and noradrenergic compounds (e.g. WO 00/71549), 5HT agonists e.g. 1-(3-ethylbenzofuran-7-yl)piperazine oxalic acid salt (WO 01/09111), bombesin agonists, galanin antagonists, growth hormone (e.g. human growth hormone), growth hormone-releasing compounds (6-benzyloxy-1-(2-diisopropylaminoethylcarbamoyl)-3,4-dihydro-1H-isoquinoline-2-carboxylic acid tertiary butyl ester (WO 01/85695)), TRH agonists (see, for example, EP 0 462 884), uncoupling protein 2 or 3 modulators, leptin agonists (see, for example, Lee, Daniel W.; Leinung, Matthew C.; Rozhayskaya-Arena, Marina; Grasso, Patricia. Leptin agonists as a potential approach to the treatment of obesity. Drugs of the Future (2001), 26(9), 873-881), DA agonists (bromocriptine, Doprexin), lipase/amylase inhibitors (e.g. WO 00/40569), PPAR modulators (e.g. WO 00/78312), RXR modulators or TR-β agonists.

In one embodiment of the invention, the other active ingredient is leptin; see, for example, "Perspectives in the therapeutic use of leptin", Salvador, Javier; Gomez-Ambrosi, Javier; Fruhbeck, Gema, Expert Opinion on Pharmacotherapy (2001), 2(10), 1615-1622.

In one embodiment, the other active ingredient is dexamphetamine or amphetamine.

In one embodiment, the other active ingredient is fenfluramine or dexfenfluramine.

In another embodiment, the other active ingredient is sibutramine.

In one embodiment, the other active ingredient is orlistat.

In one embodiment, the other active ingredient is mazindol or phentermine.

In a further embodiment, the other active ingredient is rimonabant.

In one embodiment, the compounds of the formula I are administered in combination with bulking agents, preferably insoluble bulking agents (see, for example, carob/Caromax® (Zunft H J; et al., Carob pulp preparation for treatment of hypercholesterolemia, ADVANCES IN THERAPY (2001 September-October), 18(5), 230-6.) Caromax is a carob-containing product from Nutrinova, Nutrition Specialties & Food Ingredients GmbH, Industriepark Hochst, 65926 Frankfurt/Main)). Combination with Caromax® is possible in one preparation or by separate administration of compounds of the formula I and Caromax®. Caromax® can in this connection also be administered in the form of food products such as, for example, in bakery products or muesli bars.

It will be appreciated that every suitable combination of the compounds of the invention with one or more of the aforementioned compounds and optionally one or more other pharmacologically active substances is regarded as falling within the protection conferred by the present invention.

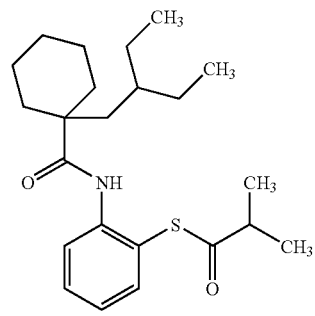

JTT-705

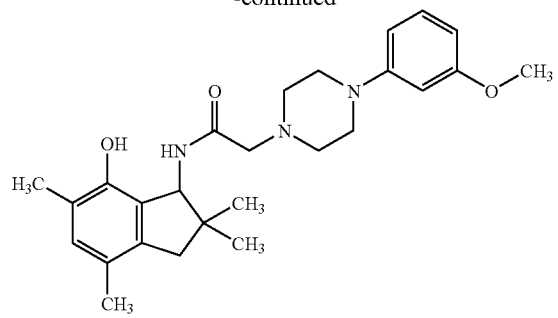
OPC-14117
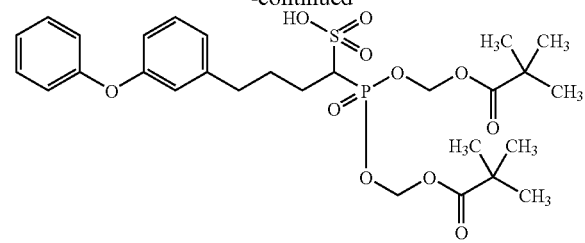
BMS-188494
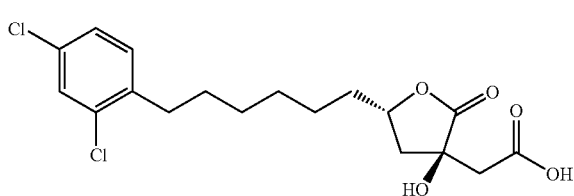
SB-204990
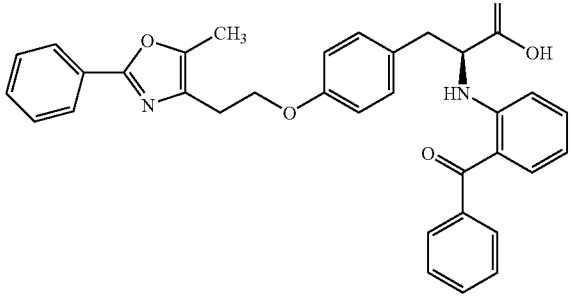
GI 262570
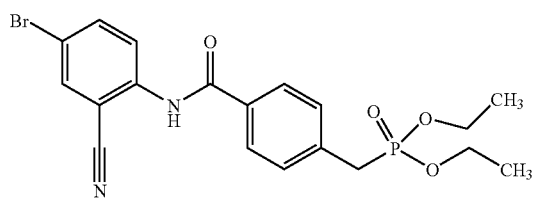
NO-1886
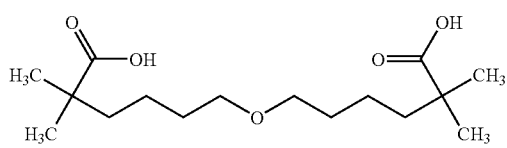
CI-1027
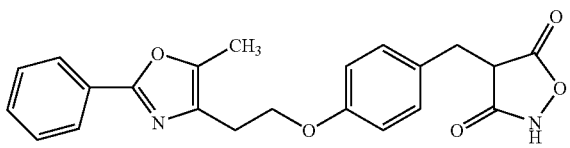
JTT-501
The examples detailed below serve to illustrate the invention but without restricting it, however.
| Example No. | Formula | Mass spectrometry data |
|---|---|---|
| 1 | 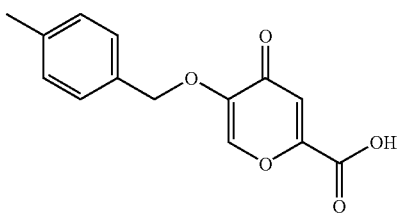 | MS(ESI⁺) 141.04 |
| 2 | 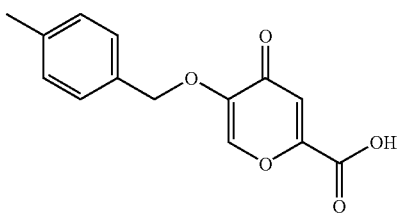 [SMILES: Cc1ccc(COc2coc(C(=O)O)cc2=O)cc1] | MS(ESI⁺) 261.12 |

-continued

| Example No. | Formula | Mass spectrometry data |
|---|---|---|
| 3 | | MS(ESI⁻) 245.54 |
| 4 | | MS(ESI⁺) 197.11 |
| 5 | | MS(ESI⁺) 227.15 |
| 6 | | MS(ESI⁺) 213.11 |
| 7 | | MS(ESI⁺) 265.22 |
| 8 | | MS(ESI⁺) 292.13 |
| 9 | | |

-continued
| Example No. | Formula | Mass spectrometry data |
|---|---|---|
| 10 | 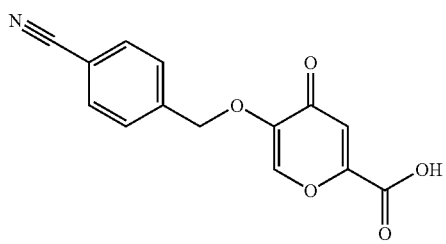 [SMILES: N#Cc1ccc(COc2coc(C(=O)O)cc2=O)cc1] | MS(ESI⁻) 270.41 |
| 11 | 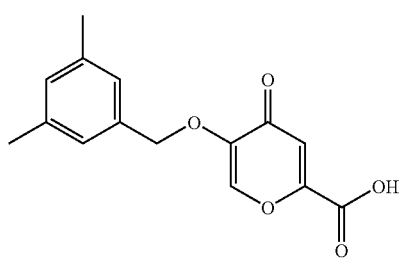 [SMILES: Cc1cc(C)cc(COc2coc(C(=O)O)cc2=O)c1] | MS(ESI⁺) 275.14 |
| 12 | 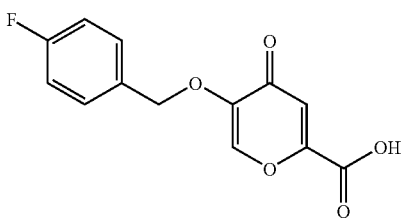 [SMILES: O=C(O)c1cc(=O)c(OCc2ccc(F)cc2)co1] | MS(ESI⁻) 263.36 |
| 13 | 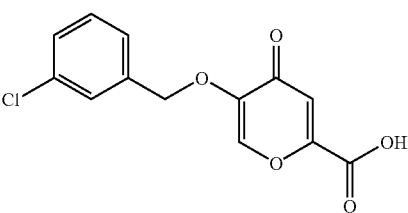 [SMILES: O=C(O)c1cc(=O)c(OCc2cccc(Cl)c2)co1] | MS(ESI⁻) 279.32 |
| 14 | 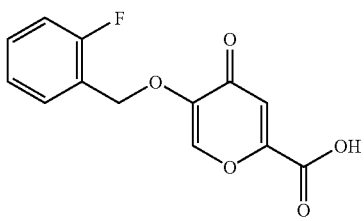 [SMILES: O=C(O)c1cc(=O)c(OCc2ccccc2F)co1] | MS(ESI⁻) 263.29 |
| 15 | 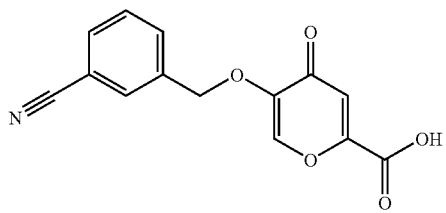 [SMILES: N#Cc1cccc(COc2coc(C(=O)O)cc2=O)c1] | MS(ESI⁻) 270.28 |

-continued
| Example No. | Formula | Mass spectrometry data |
|---|---|---|
| 16 | 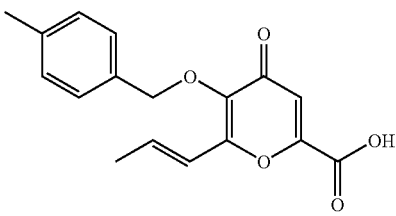 | MS(ESI$^+$) 345.10 (M + HCOO$^-$) |
| 17 | 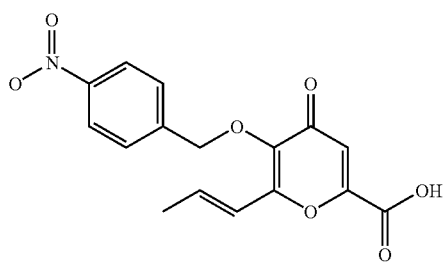 | |
| 18 | 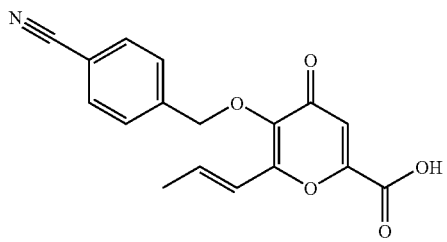 [SMILES: C/C=C/c1oc(C(=O)O)cc(=O)c1OCc1ccc(C#N)cc1] | |
| 19 | 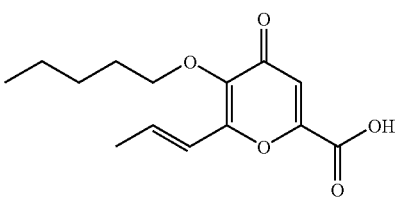 [SMILES: C/C=C/c1oc(C(=O)O)cc(=O)c1OCCCCC] | MS(ESI$^+$) 267.12 |
| 20 | 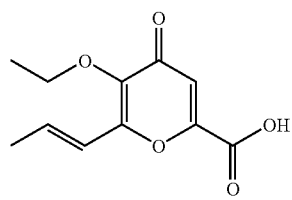 [SMILES: C/C=C/c1oc(C(=O)O)cc(=O)c1OCC] | |
| 21 | 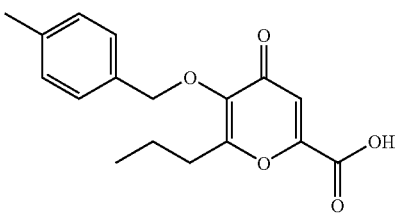 [SMILES: CCCc1oc(C(=O)O)cc(=O)c1OCc1ccc(C)cc1] | MS(ESI$^+$) 303.13 |

-continued
| Example No. | Formula | Mass spectrometry data |
|---|---|---|
| 22 | 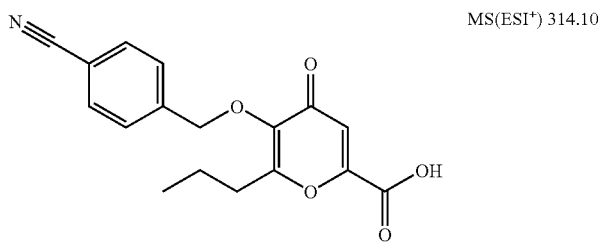 | MS(ESI+) 314.10 |
| 23 | 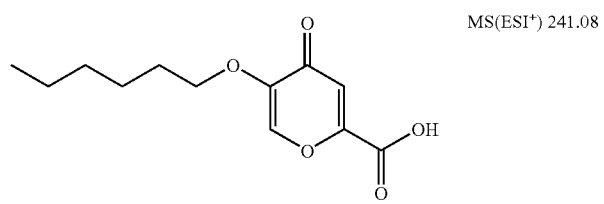 | MS(ESI+) 241.08 |
| 24 | 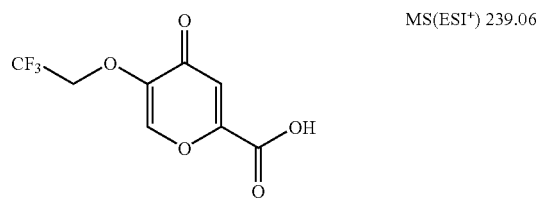 | MS(ESI+) 239.06 |
| 25 | 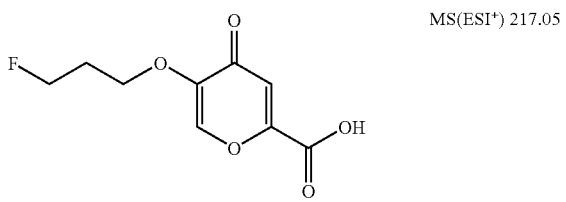 | MS(ESI+) 217.05 |
| 26 | 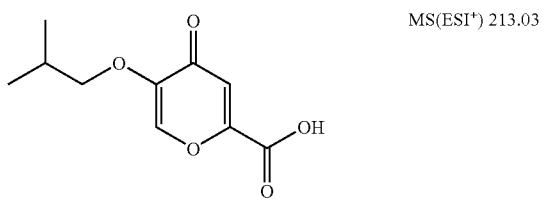 | MS(ESI+) 213.03 |
| 27 | 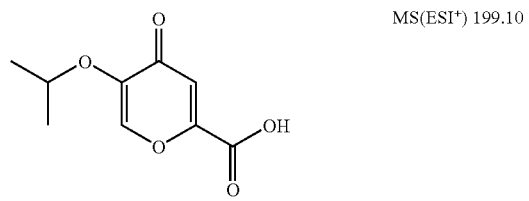 | MS(ESI+) 199.10 |
| 28 | 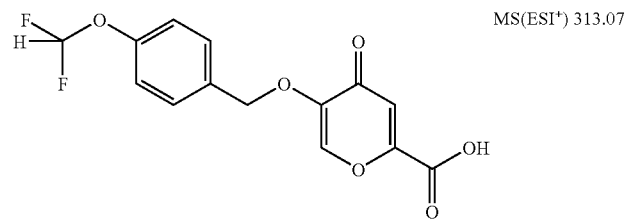 | MS(ESI+) 313.07 |

-continued

| Example No. | Formula | Mass spectrometry data |
|---|---|---|
| 29 | (4-CF₃-benzyl)oxy-4-oxo-4H-pyran-2-carboxylic acid | MS(ESI⁺) 315.22 |
| 30 | (4-ethyl-benzyl)oxy-4-oxo-4H-pyran-2-carboxylic acid | MS(ESI⁺) 275.19 |
| 31 | (4-chloro-benzyl)oxy-4-oxo-4H-pyran-2-carboxylic acid | MS(ESI⁺) 281.05 |
| 32 | (4-isopropyl-benzyl)oxy-4-oxo-4H-pyran-2-carboxylic acid | MS(ESI⁺) 289.13 |
| 33 | (4-CF₃O-benzyl)oxy-4-oxo-4H-pyran-2-carboxylic acid | MS(ESI⁺) 331.02 |
| 34 | 4-cyanobenzoyloxy-4-oxo-4H-pyran-2-carboxylic acid | MS(ESI⁺) 569.04 (2M − H⁺) |

-continued
| Example No. | Formula | Mass spectrometry data |
|---|---|---|
| 35 | 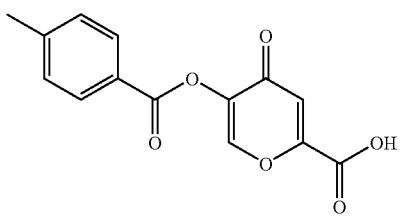 [SMILES: Cc1ccc(C(=O)Oc2coc(C(=O)O)cc2=O)cc1] | MS(ESI$^+$) 275.10 |
| 36 | 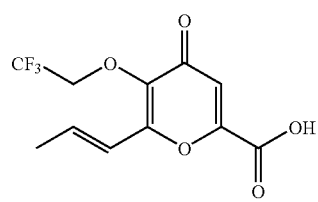 [SMILES: C/C=C/c1oc(C(=O)O)cc(=O)c1OCC(F)(F)F] | MS(ESI$^+$) 279.05 |
| 37 | 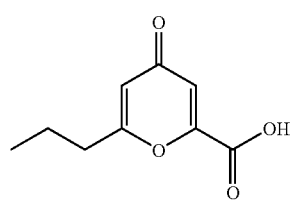 | MS(ESI$^+$) 183.11 |
| 38 | 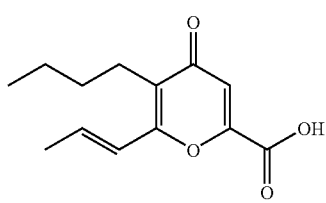 [SMILES: C/C=C/c1oc(C(=O)O)cc(=O)c1CCCC] | MS(ESI$^+$) 237.16 |
| 39 | 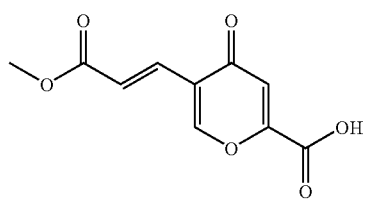 | MS(ESI$^+$) 266.10 (M + CH$_3$CN + H$^+$) |
| 40 | 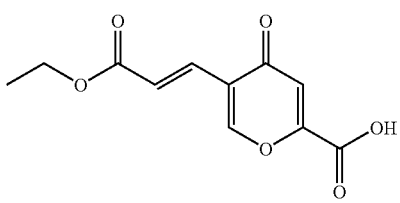 [SMILES: CCOC(=O)/C=C/c1coc(C(=O)O)cc1=O] | MS(ESI$^+$) 239.09 |
| 41 | 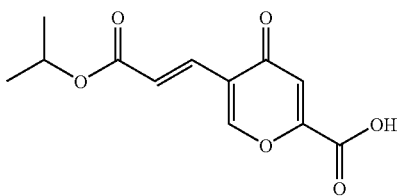 [SMILES: CC(C)OC(=O)/C=C/c1coc(C(=O)O)cc1=O] | MS(ESI$^-$) 251.17 |

-continued
| Example No. | Formula | Mass spectrometry data |
|---|---|---|
| 42 | 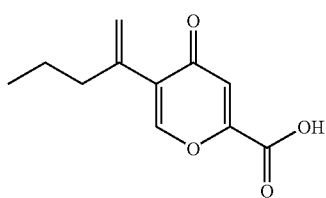 | MS(ESI+) 209.09 |
| 43 | 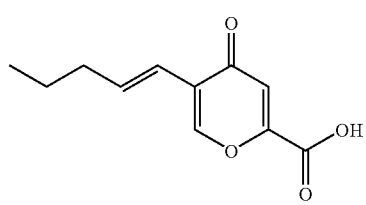 | MS(ESI+) 209.09 |
| 44 | 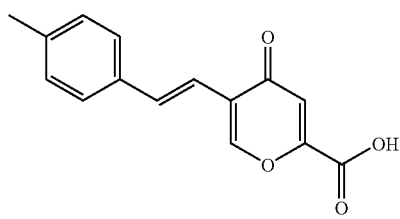 [SMILES: Cc1ccc(/C=C/c2coc(C(=O)O)cc2=O)cc1] | MS(ESI+) 257.16 |
| 45 | 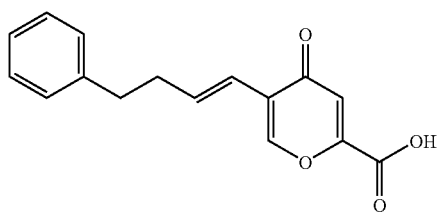 [SMILES: O=C(O)c1cc(=O)c(/C=C/CCc2ccccc2)co1] | MS(ESI+) 271.12 |
| 46 | 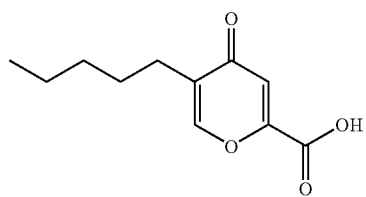 | MS(ESI+) 252.12 (M + CH$_3$CN + H$^+$) |
| 47 | 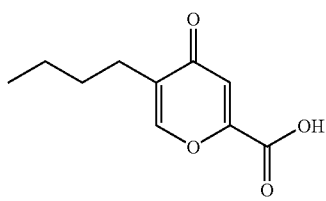 | MS(ESI+) 197.13 |
| 48 | 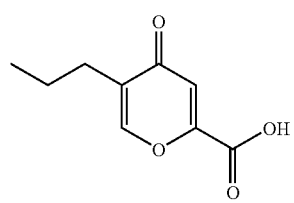 | MS(ESI+) 183.09 |

-continued

| Example No. | Formula | Mass spectrometry data |
|---|---|---|
| 49 | | MS(ESI⁺) 252.20 (M + CH₃CN + H⁺) |
| 50 | | MS(ESI⁺) 197.10 |
| 51 | | MS(ESI⁺) 238.11 (M + CH₃CN + H⁺) |
| 52 | | MS(ESI⁺) 181.15 |

The compounds of the formula I are suitable for the treatment of the metabolic syndrome (see Datamonitor November 2002, chapter 2, pages 19-32), for prediabetes treatment and for the prophylaxis of type 2 diabetes. They are particularly suitable for the treatment of diabetic dyslipidemia. Diabetic dyslipidemia is manifested by an elevation of plasma triglycerides, a reduction in HDL cholesterol and frequently in elevated LDL levels. Owing to the increased occurrence of small, dense LDL cholesterol particles of high atherogenic potency, diabetic dyslipidemia is a serious cardiovascular risk factor.

These compounds are further suitable for the treatment and/or prevention of 1.
- disorders of fatty acid metabolism and glucose utilization disorders
- disorders in which insulin resistance is involved
- hyperglycemia,
- improvement in insulin resistance,
- improvement in glucose tolerance,
- protection of the pancreatic β cells
- prevention of macro- and microvascular disorders
- dyslipidemias and their sequelae such as, for example, atherosclerosis, coronary heart disease, cerebrovascular disorders etc. in particular such as (but not restricted thereto)
- obesity (excess weight), including abdominal obesity
- thromboses, hypercoagulable and prothrombotic stages (arterial and venous)
- high blood pressure
- heart failure such as, for example, (but not restricted thereto), following myocardial infarction, hypertensive heart disease or cardiomyopathy 2. further disorders or conditions in which for example inflammatory reactions or cell differentiation are involved:
- atherosclerosis such as, for example (but not restricted thereto), coronary sclerosis including angina pectoris or myocardial infarction, stroke
- vascular restenosis or reocclusion
- chronic inflammatory bowel diseases such as, for example, Crohn's disease and ulcerative colitis
- pancreatitis
- other inflammatory conditions
- retinopathy
- adipose cell tumors
- adipose cell carcinomas such as, for example, liposarcomas
- solid tumors and neoplasms such as, for example (but not restricted thereto), carcinomas of the gastrointestinal tract, of the liver, of the biliary tract and of the pancreas, endocrine tumors, carcinomas of the lung, of the kidney and the urinary tract, of the genital tract, prostate carcinomas etc.
- acute and chronic myeloproliferative disorders and lymphomas
- angiogenesis
- neurodegenerative disorders
- Alzheimer's disease
- multiple sclerosis Parkinson's disease
erythemato-squamous dermatoses such as, for example, psoriasis
acne vulgaris
other skin disorders and dermatological conditions modulated by PPAR
eczemas and neurodermatitis
dermatitis such as, for example, seborrheic dermatitis or photodermatitis
keratitis and keratoses such as, for example, seborrheic keratoses, senile keratoses, actinic keratosis, photo-induced keratoses or keratosis follicularis
keloids and keloid prophylaxis
warts, including condylomata or condylomata acuminata
human papilloma viral (HPV) infections such as, for example, venereal warts, viral warts such as, for example, molluscum contagiosum, leukoplakia
papular dermatoses such as, for example, lichen planus
skin cancer such as, for example, basal-cell carcinomas, melanomas or cutaneous T-cell lymphomas
localized benign epidermal tumors such as, for example, keratoderma, epidermal naevi
chilblains
high blood pressure
syndrome X
polycystic ovary syndrome (PCOS)
asthma
osteoarthritis
lupus erythematosus (LE) or inflammatory rheumatic disorders such as, for example, rheumatoid arthritis
vasculitis
wasting (cachexia)
gout
ischemia/reperfusion syndrome
acute respiratory distress syndrome (ARDS)

The compounds of the formula I can be formulated for example in the following preparations:

EXAMPLE A

Soft gelatin capsules containing 100 mg of active ingredient per capsule:

|  | per capsule |
| --- | --- |
| active ingredient | 100 mg |
| triglyceride mixture fractionated from coconut fat | 400 mg |
| capsule contents | 500 mg |

EXAMPLE B

Emulsion containing 60 mg of active ingredient per 5 ml:

|  | per 100 ml of emulsion |
| --- | --- |
| active ingredient | 1.2 g |
| neutral oil | q.s. |
| sodium carboxymethylcellulose | 0.6 g |
| polyoxyethylene stearate | q.s. |
| glycerol, pure | 0.2 to 2.0 g |
| flavoring | q.s. |
| water (deionized or distilled) | ad 100 ml |

EXAMPLE C

Rectal drug form containing 40 mg of active ingredient per suppository:

|  | per suppository |
| --- | --- |
| active ingredient | 40 mg |
| suppository base | ad 2 g |

EXAMPLE D

Tablets containing 40 mg of active ingredient per tablet:

|  | per tablet |
| --- | --- |
| lactose | 600 mg |
| corn starch | 300 mg |
| soluble starch | 20 mg |
| magnesium stearate | 40 mg |
|  | 1000 mg |

EXAMPLE E

Coated tablets containing 50 mg of active ingredient per coated tablets:

|  | per coated tablet |
| --- | --- |
| active ingredient | 50 mg |
| corn starch | 100 mg |
| lactose | 60 mg |
| sec. calcium phosphate | 30 mg |
| soluble starch | 5 mg |
| magnesium stearate | 10 mg |
| colloidal silica | 5 mg |
|  | 260 mg |

EXAMPLE F

The following formulations are suitable for producing the contents of hard gelatin capsules:

| a) | active ingredient | 100 mg |
| --- | --- | --- |
|  | corn starch | 300 mg |
|  |  | 400 mg |
| b) | active ingredient | 140 mg |
|  | lactose | 180 mg |
|  | corn starch | 180 mg |
|  |  | 500 mg |

EXAMPLE G

Drops can be produced using the following formulation (100 mg of active ingredient in 1 ml=20 drops):

| | |
|---|---|
| active ingredient | 10 g |
| methyl benzoate | 0.07 g |
| ethyl benzoate | 0.03 g |
| ethanol, 96% | 5 ml |
| demineralized water | ad 100 ml |

The activity of the compounds of the formula I was tested as follows:

Biological Test Model:

The effect was tested on the whole animal (mouse, rat, hamster or dog), after a fasting period (e.g. of about 16 hours the substance is administered (e.g. p.o., iv., i.p., s.c.) and, with or without additional stimulation of endogenous lipolysis (e.g. by a bolus injection of 2 mg/kg i.p. isoprenaline), the effect of the test substance on lipolysis is determined on the basis of the liberated free fatty acids (FFA), glycerol and triglycerides by obtaining a blood sample (e.g. by retroorbital blood sampling) e.g. 15 min, 30, 60, 120 etc minutes after p.o. administration, and analyzing by standard methods of clinical chemistry (e.g. L. Thomas: Labor and Diagnose, 2nd edition, Medizinische Verlagsgesellschaft, Marburg/L. 1984; ISBN 3-921320-10-9)). The inhibition of lipolysis by the inhibitors is analyzed by comparing with the rate of lipolysis in correspondingly treated control animals.

Example 1 was administered in a dose of 3 mg/kg po, whereby the lipolysis was distinctly reduced, as it was possible to show from the reduction in free fatty acids (FFA), glycerol and triglycerides.

| FFA [mmol/l] | | |
|---|---|---|
| Time | Control n = 14 | 3 mg/kg n = 7 |
| 0 | 0.54 | 0.55 |
| 15 min | 0.59 | 0.22 |
| 30 min | 0.74 | 0.14 |
| 60 min | 0.61 | 0.16 |
| 120 min | 0.75 | 0.28 |

| Glycerol [μmol/l] | | |
|---|---|---|
| Time | Control n = 14 | 3 mg/kg n = 7 |
| 0 | 109 | 117 |
| 15 min | 94 | 55 |
| 30 min | 129 | 43 |
| 60 min | 99 | 43 |
| 120 min | 126 | 74 |

| Triglycerides [mmol/l] | | |
|---|---|---|
| Time | Control n = 16 | 3 mg/kg n = 7 |
| 0 | 0.49 | 0.53 |
| 15 min | 0.46 | 0.48 |
| 30 min | 0.41 | 0.28 |
| 60 min | 0.39 | 0.21 |
| 120 min | 0.46 | 0.25 |

Example 47 was administered in a dose of 1 mg/kg po, whereby the lipolysis was distinctly reduced, as it was possible to show from the reduction in free fatty acids (FFA), glycerol and triglycerides.

| FFA [mmol/l] | | |
|---|---|---|
| Time | Control n = 6 | 1 mg/kg n = 6 |
| 0 | 0.80 | 0.84 |
| 30 min | 0.50 | 0.25 |
| 60 min | 0.56 | 0.37 |
| 120 min | 0.59 | 0.41 |

| Glycerol [μmol/l] | | |
|---|---|---|
| Time | Control n = 6 | 1 mg/kg n = 6 |
| 0 | 160 | 162 |
| 30 min | 103 | 41 |
| 60 min | 104 | 55 |
| 120 min | 106 | 70 |

| Triglycerides [mmol/l] | | |
|---|---|---|
| Time | Control n = 6 | 1 mg/kg n = 6 |
| 0 | 0.66 | 0.84 |
| 30 min | 0.87 | 0.25 |
| 60 min | 0.67 | 0.37 |
| 120 min | 0.56 | 0.41 |

Example 48 was administered in a dose of 10 mg/kg po, whereby the lipolysis was distinctly reduced, as it was possible to show from the reduction in free fatty acids (FFA), glycerol and triglycerides.

| FFA [mmol/l] | | |
|---|---|---|
| Time | Control n = 16 | 10 mg/kg n = 6 |
| 0 | 0.53 | 0.51 |
| 30 min | 0.49 | 0.19 |
| 60 min | 0.48 | 0.19 |
| 120 min | 0.49 | 0.16 |

| Glycerol [μmol/l] | | |
|---|---|---|
| Time | Control n = 16 | 10 mg/kg n = 6 |
| 0 | 115 | 100 |
| 30 min | 97 | 35 |
| 60 min | 89 | 26 |
| 120 min | 91 | 24 |

| Triglycerides [mmol/l] | | |
|---|---|---|
| Time | Control n = 16 | 10 mg/kg n = 6 |
| 0 | 0.35 | 0.41 |
| 30 min | 0.45 | 0.36 |
| 60 min | 0.40 | 0.25 |
| 120 min | 0.35 | 0.27 |

Example 50 was administered in a dose of 3 mg/kg po, whereby the lipolysis was distinctly reduced, as it was possible to show from the reduction in free fatty acids (FFA), glycerol and triglycerides.

| FFA [mmol/l] | | |
|---|---|---|
| Time | Control n = 12 | 3 mg/kg n = 6 |
| 0 | 0.59 | 0.64 |
| 15 min | 0.62 | 0.34 |
| 30 min | 0.59 | 0.43 |
| 60 min | 0.56 | 0.50 |
| 120 min | 0.56 | 0.52 |

| Glycerol [µmol/l] | | |
|---|---|---|
| Time | Control n = 12 | 3 mg/kg n = 6 |
| 0 | 130 | 127 |
| 15 min | 121 | 67 |
| 30 min | 121 | 82 |
| 60 min | 120 | 86 |
| 120 min | 107 | 101 |

| Triglycerides [mmol/l] | | |
|---|---|---|
| Time | Control n = 12 | 3 mg/kg n = 6 |
| 0 | 0.44 | 0.47 |
| 15 min | 0.48 | 0.39 |
| 30 min | 0.56 | 0.36 |
| 60 min | 0.55 | 0.58 |
| 120 min | 0.46 | 0.71 |

"n" stands for the number of animals. Wistar rats were tested.

Agonists of the G-protein-coupled receptor HM74a (GPR109a) cause a descrease of cyclic adenosine monophosphate (cAMP) and inhibition of lipolysis in adipocytes (S. Offermanns, *Trends in Pharm Sciences* 2006, 27, 384-390).

Compounds which activate the receptor HM74a are suitable for treating diseases modulated by HM74a agonists.

The activity of the compounds of the formula I was tested in the following assays:

In vitro functional assays with recombinant cells

Function-testing assays were carried out by means of the FLIPR technique ("Fluorescence Imaging Plate Reader", Molecular Devices Corp.). For this purpose, agonist-induced changes in the intracellular concentration of $Ca^{2+}$ in recombinant HEK293 cells which express both the GPCR HM74A (niacin receptor) and the hybrid G-protein Gα6qi4myr (see, for example, DE patent application 10033353) were determined.

For the investigations, cells were seeded into 96-well microtiter plates (60 000 cells/well) and allowed to grow overnight. The medium was removed and the cells were incubated in buffer which contained the fluorescent dye Fluo-4. After this loading with dye, the cells were washed, test substance was added, and changes in the intracellular $Ca^{2+}$ concentration were measured in the FLIPR apparatus. Results have been shown as percentage change relative to the control (0%: no test substance added; 100%:1 µM reference agonist niacin added), used to calculate dose/activity plots and EC50 values determined.

TABLE 2

| Biological activity | |
|---|---|
| Example No. | EC50 (HM74a) µM |
| 1 | 0.09 |
| 2 | 4.12 |
| 3 | 28.80 |
| 4 | 29.94 |
| 5 | 1.20 |
| 6 | 52.87 |
| 7 | 62.84 |
| 8 | 36.85 |
| 9 | 43.37 |
| 10 | 14.74 |
| 11 | 31.23 |
| 12 | 49.49 |
| 13 | 19.50 |
| 14 | 12.12 |
| 15 | 67.13 |
| 16 | 0.10 |
| 17 | 0.24 |
| 18 | 0.36 |
| 19 | 0.39 |
| 20 | 0.73 |
| 21 | 4.40 |
| 22 | 45.03 |
| 23 | 34.25 |
| 24 | 1.00 |
| 25 | 0.76 |
| 26 | 45.27 |
| 27 | 4.61 |
| 28 | 1.81 |
| 29 | 45.07 |
| 30 | 3.24 |
| 31 | 7.43 |
| 32 | 1.48 |
| 33 | 22.36 |
| 34 | 0.31 |
| 35 | 1.19 |
| 36 | 0.07 |
| 37 | 66.66 |
| 38 | 0.14 |
| 39 | 1.19 |
| 40 | 1.19 |
| 41 | 6.87 |
| 42 | 6.60 |
| 43 | 1.03 |
| 44 | 4.83 |
| 45 | 10.85 |
| 46 | 0.01 |
| 47 | 0.01 |
| 48 | 0.05 |
| 49 | 0.21 |
| 50 | 0.16 |
| 51 | 0.22 |
| 52 | 2.69 |

Synthesis:

The compound of Example 1 was purchased from a chemicals merchant (ABCR GmbH KG, Karlsruhe, Germany).

Synthesis of 5-(4-methylbenzyloxy)-4-oxo-4H-pyran-2-carboxylic acid (Example 2)

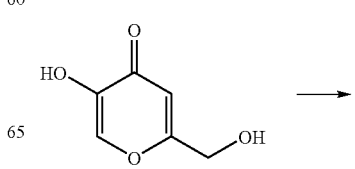

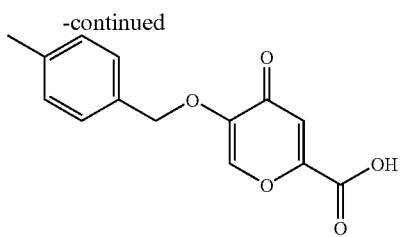

500 mg of 5-hydroxy-2-hydroxymethylpyran-4-one (koji acid) were dissolved in 20 ml of DMF, 0.47 ml of 4-methylbenzyl bromide and 0.97 g of potassium carbonate were added and the mixture was stirred at room temperature for 17 h. 50 ml of dichloromethane were added, and the reaction solution was extracted with 70 ml of a saturated solution of ammonium chloride in water. The organic phase was separated off and concentrated on a rotary evaporator. The crude product was dissolved in 100 ml of acetonitrile, and 2.4 ml of a solution of 25 g of $CrO_3$ and 25 ml of $H_2SO_4$ in 100 ml of water were added. After 1.5 h, 100 ml of methyl tert-butyl ether were added to the reaction solution. The reaction solution was then extracted 5 times with in each case 100 ml of a 1 molar HCl solution. The organic phase was dried over magnesium sulfate and concentrated on a rotary evaporator. The crude product was then purified by HPLC (Agilent-Prep.-C18, mobile phase MeCN/$H_2O$/TFA). This gives 63 mg (0.263 mmol) of 5-(4-methylbenzyloxy)-4-oxo-4H-pyran-2-carboxylic acid as a colorless wax. LCMS: m=261.12 (M+H)$^+$ The compounds of examples 3-15 and 23-35 were synthesized analogously to this general procedure starting with koji acid.

Synthesis of 5-(4-methylbenzyloxy)-4-oxo-6-propenyl-4H-pyran-2-carboxylic acid (Example 16)

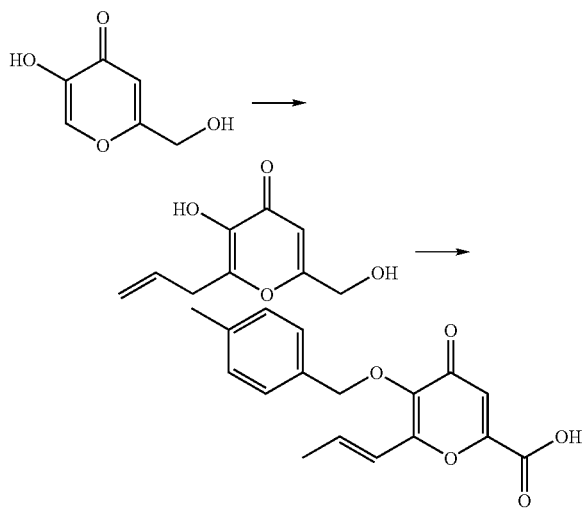

5.00 g of 5-hydroxy-2-hydroxymethylpyran-4-one (koji acid) were dissolved in 50 ml of DMF, 3.22 ml of allyl bromide and 9.73 g of potassium carbonate were added and the mixture was stirred at room temperature for 4 h. The reaction solution was reduced to a volume of 20 ml on a rotary evaporator, and 250 ml of ethyl acetate and 30 ml of water were added. The organic phase was separated off, dried over magnesium sulfate and concentrated on a rotary evaporator. The crude product was taken up in 40 ml of toluene and heated under reflux for 16 h. Cooling resulted in the formation of a colorless precipitate which was filtered off and washed with 20 ml of cold toluene. This gave 5.13 g of 2-allyl-3-hydroxy-6-hydroxymethylpyran-4-one as a colorless solid. LCMS: m=183 (M+H)$^+$. Analogously to the synthesis of the compound of Example 2, 2-allyl-3-hydroxy-6-hydroxymethylpyran-4-one was converted into 5-(4-methylbenzyloxy)-4-oxo-6-propenyl-4H-pyran-2-carboxylic acid. LCMS: m=345.10 (M+HCOO$^-$).

The compounds of examples 17-20 and 36 were synthesized analogously to this general procedure starting with koji acid.

Synthesis of 5-(4-methylbenzyloxy)-4-oxo-6-propyl-4H-pyran-2-carboxylic acid (Example 21)

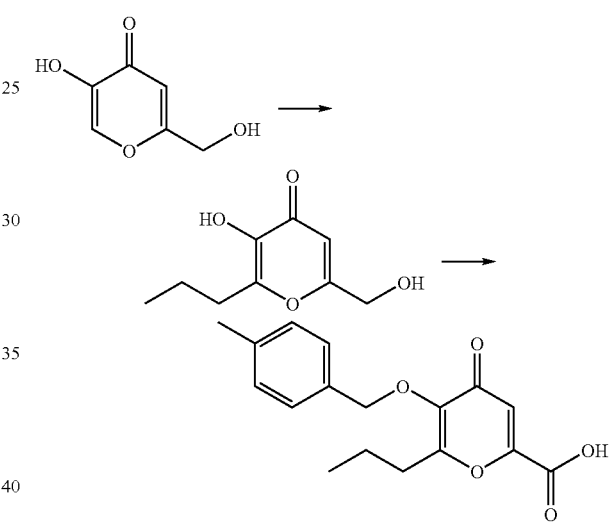

5.00 g of 5-hydroxy-2-hydroxymethylpyran-4-one (koji acid) were dissolved in 50 ml of DMF, 3.22 ml of allyl bromide and 9.73 g of potassium carbonate were added and the mixture was stirred at room temperature for 4 h. The reaction solution was reduced to a volume of 20 ml on a rotary evaporator, and 250 ml of ethyl acetate and 30 ml of water were added. The organic phase was separated off, dried over magnesium sulfate and concentrated on a rotary evaporator. The crude product was taken up in 40 ml of toluene and heated under reflux for 16 h. Cooling resulted in the formation of a colorless precipitate which was filtered off and washed with 20 ml of cold toluene. The solid obtained was dissolved in 25 ml of methanol, 350 mg of palladium on carbon (10%) were added and the mixture was stirred in an autoclave under a hydrogen atmosphere (1.5 bar) for 24 h. Palladium on carbon was filtered off, and the reaction solution was concentrated on a rotary evaporator. This gave 5.04 g of 2-propyl-3-hydroxy-6-hydroxymethylpyran-4-one as a colorless solid. LCMS: m=185 (M+H)$^+$. Analogously to the synthesis of the compound of Example 2, 2-propyl-3-hydroxy-6-hydroxymethylpyran-4-one was converted into 5-(4-methylbenzyloxy)-4-oxo-6-propyl-4H-pyran-2-carboxylic acid. LCMS: m=303.13 (M+H)$^+$.

The compound of example 22 was synthesized analogously to this general procedure starting with koji acid.

Synthesis of 5-propyl-4-oxo-4H-pyran-2-carboxylic acid (Example 48)

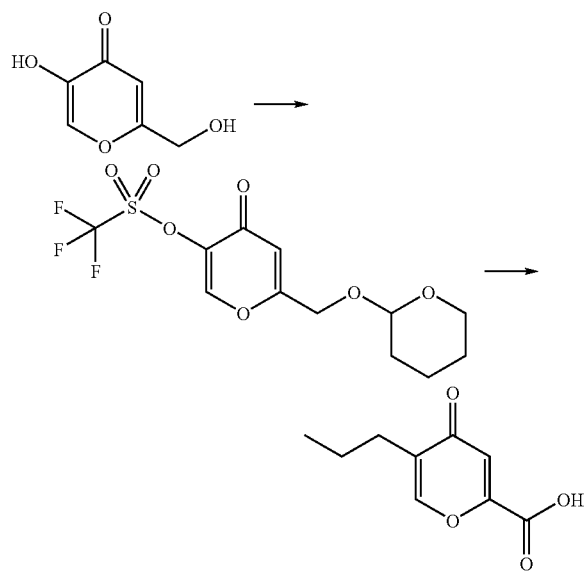

16.7 g of 5-hydroxy-2-hydroxymethylpyran-4-one (koji acid) were suspended in 200 ml of dichloromethane, and 15.8 ml of 3,4-dihydro-2H-pyran and 160 mg of toluenesulfonic acid were added. The reaction mixture was stirred at room temperature for 4 h and extracted twice with in each case 100 ml of 2-molar aqueous NaOH solution. The aqueous solution was adjusted to pH=7 using saturated aqueous $NaH_2PO_4$ solution and extracted with 200 ml of dichloromethane. The organic phase was dried over magnesium sulfate and concentrated on a rotary evaporator. The product obtained was dissolved in 200 ml of dichloromethane and cooled to 0° C., and 14 ml of pyridine and 17.6 ml of trifluoromethanesulfonic anhydride were added. After 16 h, the reaction mixture was washed with 200 ml of saturated aqueous $NH_4Cl$ solution, dried over magnesium sulfate and purified by flash chromatography (mobile phase: ethyl acetate/heptane). This gave 20.1 g of 4-oxo-6-(tetrahydropyran-2-yloxymethyl)-4H-pyran-3-yl trifluoromethanesulfonate as a colorless solid.

1.5 g of 4-oxo-6-(tetrahydropyran-2-yloxymethyl)-4H-pyran-3-yl trifluoromethanesulfonate were dissolved in 40 ml of toluene, and 47 mg of palladium(II) acetate, 260 mg of BINAP, 2.73 g of cesium carbonate and 442 mg of n-propylboronic acid were added. The reaction mixture was heated at 100° C. for 6 h. The solids were filtered off, and the reaction mixture was concentrated on a rotary evaporator. The crude product was purified by flash chromatography (mobile phase: ethyl acetate/heptane) and then dissolved in 20 ml of acetonitrile, and 2.7 ml of a solution of 25 g of $CrO_3$ and 25 ml of $H_2SO_4$ in 100 ml of water were added. After 1 h, 100 ml of methyl tert-butyl ether were added to the reaction solution. The reaction solution was then extracted twice with in each case 30 ml of a 1-molar HCl solution. The organic phase was dried over magnesium sulfate and concentrated on a rotary evaporator. The crude product was then purified by HPLC (Agilent-Prep.-C18, mobile phase $MeCN/H_2O/TFA$). This gave 194 mg (1.07 mmol) of 5-propyl-4-oxo-4H-pyran-2-carboxylic acid as a colorless solid. LCMS: m=183.09 $(M+H)^+$.

The compounds of examples 42-43 and of examples 46-47 were synthesized analogously to this general procedure starting with koji acid.

The compound 38 was synthesized analogously to this general procedure starting with 2-allyl-3-hydroxy-6-hydroxymethyl-pyran-4-one.

Synthesis of 6-propyl-4-oxo-4H-pyran-2-carboxylic acid (Example 37)

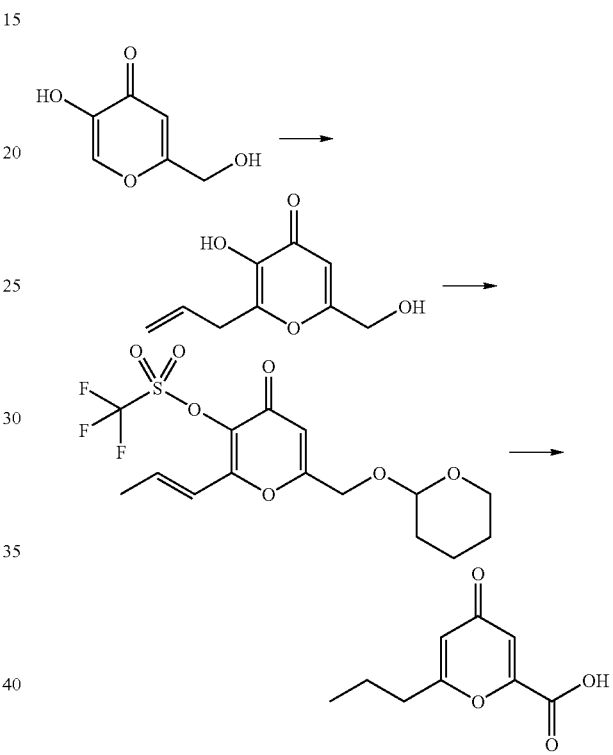

25.0 g of 2-allyl-3-hydroxy-6-hydroxymethylpyran-4-one were dissolved in 500 ml of dichloromethane, and 18.4 ml of 3,4-dihydro-2H-pyran and 182 mg of toluenesulfonic acid were added. The reaction mixture was stirred at room temperature for 2 h and extracted 2 times with in each case 100 ml of 2-molar aqueous NaOH solution. The aqueous solution was adjusted to pH=7 with saturated aqueous $NaH_2PO_4$ solution and extracted with 400 ml of dichloromethane. The organic phase was dried over magnesium sulfate and concentrated on a rotary evaporator. The product obtained was suspended in 222 ml of dichloromethane and cooled to 0° C., and 12.8 ml of pyridine and 22.2 ml of trifluoromethanesulfonic anhydride were added. After 2 h, the reaction mixture was washed with 200 ml of saturated aqueous $NH_4Cl$ solution, dried over magnesium sulfate and purified by flash chromatography (mobile phase: ethyl acetate/heptane). This gave 15.8 g of 4-oxo-24(E)-propenyl)-6-(tetrahydropyran-2-yloxymethyl)-4H-pyran-3-yl trifluoromethanesulfonate as a colorless solid.

7.00 g of 4-oxo-24(E)-propenyl)-6-(tetrahydropyran-2-yloxymethyl)-4H-pyran-3-yl trifluoromethanesulfonate were dissolved in 40.8 ml of DMF, and 75.8 mg of palladium (II) acetate, 154 mg of tri-(o-tolyl)-phosphine, 7.07 ml of triethylamine and 0.64 ml of formic acid were added. The reaction mixture was heated at 60° C. for 1 h.

The solids were filtered off, and the reaction mixture was concentrated on a rotary evaporator. The crude product was purified by flash chromatography (mobile phase: ethyl acetate/heptane) and then dissolved in 46.7 ml of acetonitrile, and 2.0 ml of a solution of 25 g of $CrO_3$ and 25 ml of $H_2SO_4$ in 100 ml of water were added. After 1 h, 100 ml of methyl tert-butyl ether were added to the reaction solution. The reaction solution was then extracted 3 times with in each case 30 ml of a 1-molar HCl solution. The organic phase was dried over magnesium sulfate and concentrated on a rotary evaporator. The crude product was then purified by HPLC (Agilent-Prep.-C18, mobile phase MeCN/$H_2O$/TFA). This gives 7 mg of 6-propyl-4-oxo-4H-pyran-2-carboxylic acid as a colorless solid. LCMS: m=183.11 $(M+H)^+$.

Synthese von 5-((E)-2-ethoxycarbonylvinyl)-4-oxo-4H-pyran-2-carboxylic acid (Example 40)

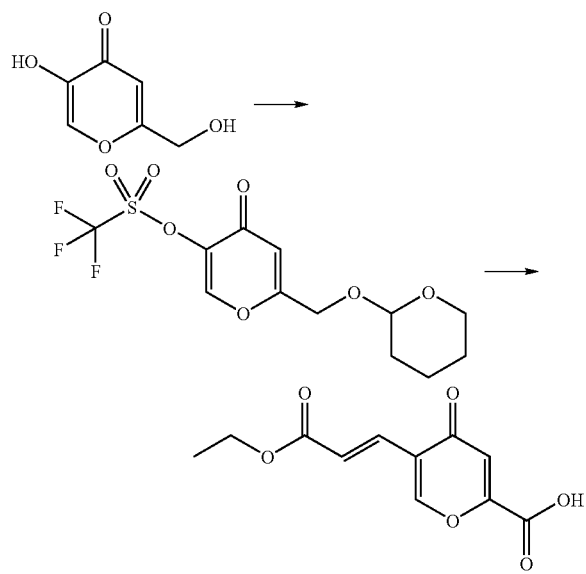

3.00 g of 4-oxo-6-(tetrahydropyran-2-yloxymethyl)-4H-pyran-3-yl trifluoromethanesulfonate are dissolved in 200 ml of THF, and 1.09 g of ethyl acrylate, 37.6 mg of palladium(II) acetate, 3.46 ml of triethylamine and 102 mg of tri-(o-tolyl)-phosphine were added. The solution was stirred at 80° C. for 6 h. Precipitates formed were removed by filtration. The organic phase was concentrated on a rotary evaporator and purified by flash chromatography (mobile phase: ethyl acetate/heptane). This gives 507 mg of 5-((E)-2-ethoxycarbonylvinyl)-2-(tetrahydropyran-2-yloxymethyl)-pyran-4-one which were dissolved in 15 ml of acetonitrile, and 1.80 ml of a solution of 25 g of $CrO_3$ and 25 ml of $H_2SO_4$ in 100 ml of water were added. After 1 h, 60 ml of methyl tert-butyl ether were added to the reaction solution. The reaction solution was then extracted 2 times with in each case 100 ml of a 1-molar HCl solution. The organic phase was dried over magnesium sulfate and concentrated on a rotary evaporator. The crude product was then purified by HPLC (Agilent-Prep.-C18, mobile phase MeCN/$H_2O$/TFA). This gives 110 mg of 5-((E)-2-ethoxycarbonylvinyl)-4-oxo-4H-pyran-2-carboxylic acid as a colorless solid. LCMS: m=239.09 $(M+H)^+$.

The compounds of examples 39, 41, 44 and 45 were synthesized analogously to this general procedure starting with koji acid.

Synthesis of 5-(3-methylbutyl)-4-oxo-4H-pyran-2-carboxylic acid (Example 49)

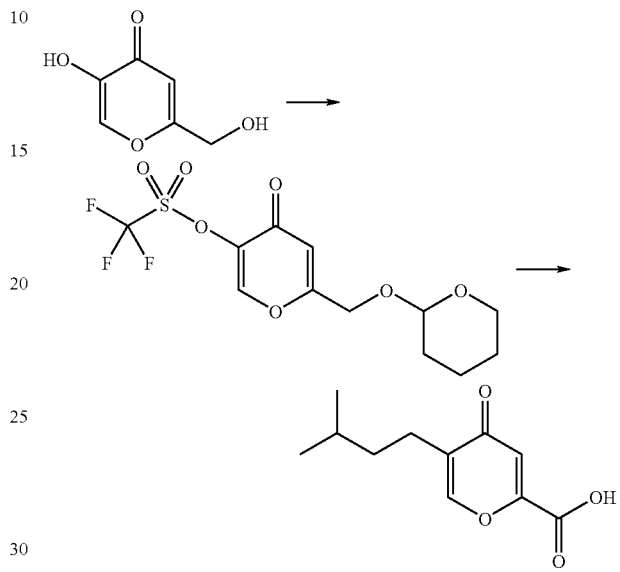

2.28 g of 4-oxo-6-(tetrahydropyran-2-yloxymethyl)-4H-pyran-3-yl trifluoromethanesulfonate are dissolved in 35 ml of THF, and at 0° C. 25.46 ml of a 0.5 molar solution of 3-methylbutylzinc bromide in THF, 71.44 mg of palladium (II) acetate, 4.15 g of cesium carbonate and 396 mg of BINAP are added. The solution was stirred at RT for 1 h and then heated under reflux for 5 h. Precipitates formed were removed by filtration. The organic phase was concentrated on a rotary evaporator. The residue was taken up in 200 ml of ethyl acetate, washed with 100 ml, dried over magnesium sulfate, concentrated on a rotary evaporator and purified by flash chromatography (mobile phase: ethyl acetate/heptane). This gives 210 mg of 5-(3-methylbutyl)-2-(tetrahydropyran-2-yloxymethyl)pyran-4-one which were dissolved in 20 ml of acetonitrile, and 0.75 ml of a solution of 25 g of $CrO_3$ and 25 ml of $H_2SO_4$ in 100 ml of water were added. After 1.5 h, 100 ml of methyl tert-butyl ether were added to the reaction solution. The reaction solution was then extracted 4 times with in each case 50 ml of a 1-molar HCl solution. The organic phase was dried over magnesium sulfate and concentrated on a rotary evaporator. The crude product was then purified by HPLC (Agilent-Prep.-C18, mobile phase MeCN/$H_2O$/TFA). This gives 35 mg (0.166 mmol) of 5-(3-methylbutyl)-4-oxo-4H-pyran-2-carboxylic acid as a colorless wax. LCMS: m=252.20 $(M+H+MeCN)^+$.

The compounds of examples 49-52 were synthesized analogously to this general procedure starting with koji acid.

What is claimed is:
1. A method for reducing plasma free fatty acids, reducing plasma glycerol, reducing plasma triglycerides, or treating diabetic dyslipidemia in a patient in need thereof, said method comprising administering to said patient a compound of the formula I:

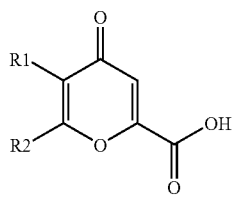

wherein:

R1 is selected from H, OH, COOH, $(C_1-C_8)$-alkyl, $(C_2-C_8)$-alkenyl, O—$(C_1-C_8)$-alkyl, and O—$(C_2-C_8)$-alkenyl, and wherein the $(C_1-C_8)$-alkyl and $(C_2-C_8)$-alkenyl radicals may be substituted by one or more groups selected from F, Cl, Br, I, $CF_3$, $NO_2$, $N_3$, CN, =O, COOH, COO$(C_1-C_6)$-alkyl, $CONH_2$, CONH$(C_1-C_6)$-alkyl, CON[$(C_1-C_6)$-alkyl]$_2$, cycloalkyl, $(C_1-C_{10})$-alkyl, $(C_2-C_6)$-alkenyl, $(C_2-C_6)$-alkynyl, O—$(C_1-C_6)$alkyl, and O—CO—$(C_1-C_6)$-alkyl, provided that the $(C_1-C_8)$-alkyl radicals are not substituted by O—$(C_1-C_6)$alkyl or O—CO—$(C_1-C_6)$-alkyl;

$PO_3H_2$, $P(O)(Oalkyl)_2$, $(C_1-C_6)$-alkylene-$P(O)(Oalkyl)_2$, O—$P(O)(OH)_2$, O—$P(O)(Oalkyl)2$, $SO_3H$, $SO_2$—$NH_2$, $SO_2NH(C_1-C_6)$-alkyl, $SO_2N[(C_1-C_6)$-alkyl]$_2$, S—$(C_1-C_6)$-alkyl, S—$(CH_2)_n$-aryl, S—$(CH_2)_n$-heterocyclyl, SO—$(C_1-C_6)$-alkyl, SO—$(CH_2)_n$-aryl, SO—$(CH_2)_n$-heterocyclyl, $SO_2$—$(C_1-C_6)$-alkyl, $SO_2$—$(CH_2)_n$-aryl, $SO_2$—$(CH_2)_n$-heterocyclyl, $SO_2$—NH$(CH_2)_n$-aryl, $SO_2$—NH$(CH_2)_n$-heterocyclyl, $SO_2$—N$((C_1-C_6)$-alkyl)$(CH_2)_n$-aryl, $SO_2$—N$((C_1-C_6)$-alkyl)$(CH_2)_n$-heterocyclyl, $SO_2$—N$((CH_2)_n$-aryl$)_2$, $SO_2$—N$((CH_2)_n$-(heterocyclyl)$)_2$ where n=0-6 and the aryl radical or heterocyclic radical may be substituted up to two times by groups selected from F, Cl, Br, OH, $CF_3$, $SF_5$, $NO_2$, CN, $OCF_3$, O—$(C_1-C_6)$-alkyl, $(C_1-C_6)$-alkyl, and $NH_2$;

$C(NH)(NH_2)$, $NH_2$, NH—$(C_1-C_6)$-alkyl, N$((C_1-C_6)$-alkyl$)_2$, $NH(C_1-C_7)$-acyl, NH—CO—$(C_1-C_6)$-alkyl, NH—COO—$(C_1-C_6)$-alkyl, NH—CO-aryl, NH—CO-heterocyclyl, NH—COO-aryl, NH—COO-heterocyclyl, NH—CO—NH—$(C_1-C_6)$-alkyl), NH—CO—NH-aryl, NH—CO—NH-heterocyclyl, N[$(C_1-C_6)$-alkyl]-CO—$(C_1-C_6)$-alkyl, N[$(C_1-C_6)$-alkyl]-COO—$(C_1-C_6)$-alkyl, N[$(C_1-C_6)$-alkyl]-CO-aryl, N[$(C_1-C_6)$-alkyl]-CO-heterocyclyl, N[$(C_1-C_6)$-alkyl]-COO-aryl, N[$(C_1-C_6)$-alkyl]-COO-heterocyclyl, N[$(C_1-C_6)$-alkyl]-CO—NH—$(C_1-C_6)$-alkyl), N[$(C_1-C_6)$-alkyl]-CO—NH-aryl, N[$(C_1-C_6)$-alkyl]-CO—NH-heterocyclyl, N[$(C_1-C_6)$-alkyl]-CO—N$((C_1-C_6)$-alkyl$)_2$, N[$(C_1-C_6)$-alkyl]-CO—N$((C_1-C_6)$-alkyl)-aryl, N[$(C_1-C_6)$-alkyl]-CO—N$((C_1-C_6)$-alkyl)-heterocyclyl, N[$(C_1-C_6)$-alkyl]-CO—N$(aryl)_2$, N[$(C_1-C_6)$-alkyl]-CO—N$(heterocyclyl)_2$, N$(aryl)$-CO—$(C_1-C_6)$-alkyl, N$(heterocyclyl)$-CO—$(C_1-C_6)$-alkyl, N$(aryl)$-COO—$(C_1-C_6)$-alkyl, N$(heterocyclyl)$-COO—$(C_1-C_6)$-alkyl, N$(aryl)$-CO-aryl, N$(heterocyclyl)$-CO-aryl, N$(aryl)$-COO-aryl, N$(heterocyclyl)$-COO-aryl, N$(aryl)$-CO—NH—$(C_1-C_6)$-alkyl, N$(heterocyclyl)$-CO—NH—$(C_1-C_6)$-alkyl, N$(aryl)$-CO—NH-aryl, N$(heterocyclyl)$-CO—NH-aryl, N$(aryl)$-CO—N$((C_1-C_6)$-alkyl$)_2$, N$(heterocyclyl)$-CO—N$((C_1-C_6)$-alkyl$)_2$, N$(aryl)$-CO—N[$(C_1-C_6)$-alkyl]-aryl, N$(heterocyclyl)$-CO—N[$(C_1-C_6)$-alkyl]-aryl, N$(aryl)$-CO—N$(aryl)_2$, N$(heterocyclyl)$-CO—N$(aryl)_2$, aryl, O—$(CH_2)_n$-aryl, O—$(CH_2)_n$-heterocyclyl, where n=0-6, where the aryl or heterocyclyl radical may be substituted by one to three groups selected from by F, Cl, Br, I, OH, $CF_3$, $NO_2$, CN, $OCF_3$, O—$(C_1-C_6)$-alkyl, $(C_1-C_6)$-alkyl, $NH_2$, $NH(C_1-C_6)$-alkyl, N$((C_1-C_6)$-alkyl$)_2$, $SF_5$, $SO_2$—$CH_3$, COOH, COO—$(C_1-C_6)$-alkyl, and $CONH_2$;

may be substituted by one to three groups selected from F, Cl, Br, I, OH, $CF_3$, $NO_2$, CN, $OCF_3$, O—$(C_1-C_6)$-alkyl, $(C_1-C_6)$-alkyl, $NH_2$, $NH(C_1-C_6)$-alkyl, N$((C_1-C_6)$-alkyl$)_2$, $SF_5$, $SO_2$—$CH_3$, COOH, COO—$(C_1-C_6)$-alkyl, and $CONH_2$; and R2 is selected from H, OH, COOH, $(C_3-C_8)$-cycloalkyl, $(C_2-C_8)$-alkenyl, O—$(C_1-C_8)$-alkyl, and O—$(C_2-C_8)$-alkenyl, and wherein the alkyl, cycloalkyl, and alkenyl radicals may be substituted by one or more groups selected from F, Cl, Br, I, $CF_3$, $NO_2$, $N_3$, CN, =O, COOH, COO$(C_1-C_6)$-alkyl, $CONH_2$, CONH$(C_1-C_6)$-alkyl, CON[$(C_1-C_6)$-alkyl]$_2$, cycloalkyl, $(C_1-C_{10})$-alkyl, $(C_2-C_6)$-alkenyl, $(C_2-C_6)$-alkynyl, O—$(C_1-C_6)$alkyl, O—CO—$(C_1-C_6)$-alkyl, O—CO—$(C_1-C_6)$-aryl, and O—CO—$(C_1-C_6)$-heterocyclyl, provided that the alkyl radicals are not substituted by O—$(C_1-C_6)$alkyl or O—CO—$(C_1-C_6)$-alkyl;

$PO_3H_2$, $P(O)(Oalkyl)_2$, $(C_1-C_6)$-alkylene-$P(O)(Oalkyl)_2$, O—$P(O)(OH)_2$, O—$P(O)(Oalkyl)2$, $SO_3H$, $SO_2$—$NH_2$, $SO_2NH(C_1-C_6)$-alkyl, $SO_2N[(C_1-C_6)$-alkyl]$_2$, S—$(C_1-C_6)$-alkyl, S—$(CH_2)_n$-aryl, S—$(CH_2)_n$-heterocyclyl, SO—$(C_1-C_6)$-alkyl, SO—$(CH_2)_n$-aryl, SO—$(CH_2)_n$-heterocyclyl, $SO_2$—$(C_1-C_6)$-alkyl, $SO_2$—$(CH_2)_n$-aryl, $SO_2$—$(CH_2)_n$-heterocyclyl, $SO_2$—NH$(CH_2)_n$-aryl, $SO_2$—NH$(CH_2)_n$-heterocyclyl, $SO_2$—N$((C_1-C_6)$-alkyl)$(CH_2)_n$-aryl, $SO_2$—N$((C_1-C_6)$-alkyl)$(CH_2)_n$-heterocyclyl, $SO_2$—N$((CH_2)_n$-aryl$)_2$, $SO_2$—N$((CH_2)_n$-(heterocyclyl)$)_2$ where n=0-6 and the aryl radical or heterocyclic radical may be substituted up to two times by groups selected from F, Cl, Br, OH, $CF_3$, $SF_5$, $NO_2$, CN, $OCF_3$, O—$(C_1-C_6)$-alkyl, $(C_1-C_6)$-alkyl, and $NH_2$;

$C(NH)(NH_2)$, $NH_2$, NH—$(C_1-C_6)$-alkyl, N$((C_1-C_6)$-alkyl$)_2$, $NH(C_1-C_7)$-acyl, NH—CO—$(C_1-C_6)$-alkyl, NH—COO—$(C_1-C_6)$-alkyl, NH—CO-aryl, NH—CO-heterocyclyl, NH—COO-aryl, NH—COO-heterocyclyl, NH—CO—NH—$(C_1-C_6)$-alkyl), NH—CO—NH-aryl, NH—CO—NH-heterocyclyl, N[$(C_1-C_6)$-alkyl]-CO—$(C_1-C_6)$-alkyl, N[$(C_1-C_6)$-alkyl]-COO—$(C_1-C_6)$-alkyl, N[$(C_1-C_6)$-alkyl]-CO-aryl, N[$(C_1-C_6)$-alkyl]-CO-heterocyclyl, N[$(C_1-C_6)$-alkyl]-COO-aryl, N[$(C_1-C_6)$-alkyl]-COO-heterocyclyl, N[$(C_1-C_6)$-alkyl]-CO—NH—$(C_1-C_6)$-alkyl), N[$(C_1-C_6)$-alkyl]-CO—NH-aryl, N[$(C_1-C_6)$-alkyl]-CO—NH-heterocyclyl, N[$(C_1-C_6)$-alkyl]-CO—N$((C_1-C_6)$-alkyl$)_2$, N[$(C_1-C_6)$-alkyl]-CO—N$((C_1-C_6)$-alkyl)-aryl, N[$(C_1-C_6)$-alkyl]-CO—N$((C_1-C_6)$-alkyl)-heterocyclyl, N[$(C_1-C_6)$-alkyl]-CO—N$(aryl)_2$, N[$(C_1-C_6)$-alkyl]-CO—N$(heterocyclyl)_2$, N$(aryl)$-CO—$(C_1-C_6)$-alkyl, N$(heterocyclyl)$-CO—$(C_1-C_6)$-alkyl, N$(aryl)$-COO—$(C_1-C_6)$-alkyl, N$(heterocyclyl)$-COO—$(C_1-C_6)$-alkyl, N$(aryl)$-CO-aryl, N$(heterocyclyl)$-CO-aryl, N$(aryl)$-COO-aryl, N$(heterocyclyl)$-COO-aryl, N$(aryl)$-CO—NH—$(C_1-C_6)$-alkyl, N$(heterocyclyl)$-CO—NH—$(C_1-C_6)$-alkyl, N$(aryl)$-CO—NH-aryl, N$(heterocyclyl)$-CO—NH-aryl, N$(aryl)$-CO—N$((C_1-C_6)$-alkyl$)_2$, N$(heterocyclyl)$-CO—N$((C_1-C_6)$-alkyl$)_2$, N$(aryl)$-CO—N[$(C_1-C_6)$-alkyl]-aryl, N$(heterocyclyl)$-CO—N[$(C_1-C_6)$-alkyl]-aryl, N$(aryl)$-CO—N$(aryl)_2$, N$(heterocyclyl)$-CO—N$(aryl)_2$, aryl, O—$(CH_2)_n$-aryl, O—$(CH_2)_n$-heterocyclyl, where n=0-6, where the aryl or heterocyclyl radical may be substituted by one to three groups selected from by F, Cl, Br, I, OH, $CF_3$, $NO_2$, CN, $OCF_3$, O—$(C_1-C_6)$-alkyl, $(C_1-C_6)$-alkyl, $NH_2$, $NH(C_1-C_6)$-alkyl, N$((C_1-C_6)$-alkyl$)_2$, $SF_5$, $SO_2$—$CH_3$, COOH, COO—$(C_1-C_6)$-alkyl, and $CONH_2$;

or R1 and R2 together form a 3- to 8-membered aryl, cycloalkyl or heterocyclyl ring, where the aryl, cycloalkyl or heterocyclyl ring may be substituted by groups selected from F, Cl, Br, I, OH, $CF_3$, $NO_2$, CN, $OCF_3$, O—$(C_1$-$C_6)$-alkyl, $(C_1$-$C_6)$-alkyl, $NH_2$, $NH(C_1$-$C_6)$-alkyl, $N((C_1$-$C_6)$-alkyl$)_2$, $SF_5$, $SO_2$—$CH_3$, COOH, COO—$(C_1$-$C_6)$-alkyl, and $CONH_2$ provided that, if R1 is OH, then R2 is not H, and if R2 is OH, then R1 is not H;

and provided that if R1 is O—$(C_1$-$C_8)$-alkyl, then R2 is not H, and if R2 is O—$(C_1$-$C_8)$-alkyl, then R1 is not H.

2. The method according to claim 1, wherein:

R1 is selected from H, OH, COOH, $(C_1$-$C_8)$-alkyl, $(C_2$-$C_8)$-alkenyl, O—$(C_1$-$C_8)$-alkyl, and O—$(C_2$-$C_8)$-alkenyl, and wherein the $(C_1$-$C_8)$-alkyl and $(C_2$-$C_8)$-alkenyl radicals may be substituted by one or more =O groups;

and

R2 is selected from H, $(C_1$-$C_8)$-alkyl, and $(C_2$-$C_8)$-alkenyl.

3. The method according to claim 1, wherein:

R1 is selected from H, OH, $(C_1$-$C_8)$-alkyl, $(C_2$-$C_4)$-alkenyl, O—$(C_1$-$C_8)$-alkyl, and O—$(C_2$-$C_4)$-alkenyl, and wherein the alkyl and alkenyl radicals may be substituted by one or more =O groups;

and

R2 is selected from H, $(C_1$-$C_8)$-alkyl, and $(C_2$-$C_4)$-alkenyl.

4. The method according to claim 1, wherein:

R1 is selected from H, OH, COOH, $(C_1$-$C_8)$-alkyl, $(C_2$-$C_8)$-alkenyl, O—$(C_1$-$C_8)$-alkyl, and O—$(C_2$-$C_8)$-alkenyl, wherein the $(C_1$-$C_8)$-alkyl and $(C_2$-$C_8)$-alkenyl radicals may be substituted by one or more groups selected from F and =O;

and

R2 is selected from H, $(C_1$-$C_8)$-alkyl, and $(C_2$-$C_8)$-alkenyl.

5. The method according to claim 1, wherein:

R1 is selected from H, OH, $(C_1$-$C_8)$-alkyl, $(C_2$-$C_4)$-alkenyl, O—$(C_1$-$C_8)$-alkyl, and O—$(C_2$-$C_8)$-alkenyl, wherein the $(C_1$-$C_8)$-alkyl and $(C_2$-$C_8)$-alkenyl radicals may be substituted by one or more groups selected from F and =O;

and

R2 is selected from H, $(C_1$-$C_8)$-alkyl, and $(C_2$-$C_4)$-alkenyl.

* * * * *